United States Patent
Ben-Yishai et al.

(10) Patent No.: US 12,079,385 B2
(45) Date of Patent: Sep. 3, 2024

(54) OPTICAL SEE THROUGH (OST) HEAD MOUNTED DISPLAY (HMD) SYSTEM AND METHOD FOR PRECISE ALIGNMENT OF VIRTUAL OBJECTS WITH OUTWARDLY VIEWED OBJECTS

(71) Applicant: ELBIT SYSTEMS LTD, Haifa (IL)

(72) Inventors: Rani Ben-Yishai, Haifa (IL); Gil Benesh, Haifa (IL)

(73) Assignee: ELBIT SYSTEMS LTD., Haifa (IL)

( * ) Notice: Subject to any disclaimer, the term of this patent is extended or adjusted under 35 U.S.C. 154(b) by 0 days.

(21) Appl. No.: 18/557,618

(22) PCT Filed: Apr. 27, 2021

(86) PCT No.: PCT/IL2021/050485
§ 371 (c)(1),
(2) Date: Oct. 27, 2023

(87) PCT Pub. No.: WO2022/229943
PCT Pub. Date: Nov. 3, 2022

(65) Prior Publication Data
US 2024/0220012 A1 Jul. 4, 2024

(51) Int. Cl.
*G06F 3/01* (2006.01)
*G02B 27/01* (2006.01)

(52) U.S. Cl.
CPC ......... *G06F 3/013* (2013.01); *G02B 27/0172* (2013.01)

(58) Field of Classification Search
USPC ............................................................ 345/8
See application file for complete search history.

(56) References Cited

U.S. PATENT DOCUMENTS 8,138,991 B2   3/2012 Rorberg
9,541,996 B1 *  1/2017 Baxter ................... G06F 3/012
(Continued)

FOREIGN PATENT DOCUMENTS

IL        271129 A       6/2021
WO   2018220631 A1    12/2018
WO   2019152619 A1     1/2019

OTHER PUBLICATIONS

Ronald Azuma et al. "Improving Static and Dynamic Registration in an Optical See-through HMD" SIGGRAPH '94: Proceedings of the 21st annual conference on Computer graphics and interactive techniques, pp. 197-204, Jul. 1994. https://doi.org/10.1145/192161.192199, 17 pgs.

(Continued)

*Primary Examiner* — Chineyere D Wills-Burns
(74) *Attorney, Agent, or Firm* — Merchant & Gould P.C.

(57) ABSTRACT

A method for irradiating an image in an optical see-through (OST) head mounted display (HMD) for viewing through, the OST HMD by a user's eye, an object having at least one of known orientation and position and orientation (O/P&O), associated with a first reference frame, the method comprising: generating and irradiating said image for appearing to said user superimposed in an aligned manner to said object, according to predetermined information, eyeball feature position data, and said O/P&O; said predetermined information relates correction data with a plurality of different respective position data values of at least one eyeball feature position of said eye; said predetermined information further includes display corrections of said electro-optical display module with respect to said position data values of said at least one eyeball feature position, with respect to a second reference frame; and said O/P&O is between said second reference and said first reference frame.

15 Claims, 15 Drawing Sheets

(56) References Cited

U.S. PATENT DOCUMENTS

| | | | |
|---|---|---|---|
| 11,397,465 B1* | 7/2022 | Mattila | G02B 27/0093 |
| 2002/0113756 A1* | 8/2002 | Tuceryan | G02B 27/017 |
| | | | 348/E13.052 |
| 2003/0025955 A1* | 2/2003 | Curtis | G11B 7/0065 |
| 2011/0187844 A1 | 8/2011 | Ogawa | |
| 2014/0078023 A1 | 3/2014 | Ikeda | |
| 2014/0331334 A1* | 11/2014 | Kamai | G06F 3/14 |
| | | | 726/28 |
| 2015/0193980 A1* | 7/2015 | Pedley | G02B 27/017 |
| | | | 345/419 |
| 2016/0080732 A1* | 3/2016 | Pedley | H04N 13/344 |
| | | | 345/8 |
| 2016/0349510 A1* | 12/2016 | Miller | H04N 13/398 |
| 2018/0053284 A1 | 2/2018 | Rodriguez | |
| 2018/0114298 A1* | 4/2018 | Malaika | G02B 27/017 |
| 2019/0108645 A1* | 4/2019 | Ben-Yishai | G06T 7/337 |
| 2020/0081530 A1* | 3/2020 | Greenberg | G06T 7/521 |
| 2020/0363867 A1* | 11/2020 | Azimi | G02B 27/0179 |
| 2020/0388054 A1* | 12/2020 | Araújo | G06T 7/85 |

OTHER PUBLICATIONS

Yuta Itoh et al. "Interaction-Free Calibration for Optical See-Through Head-Mounted Displays based on 3D Eye Localization" IEEE Symposium on 3D User Interfaces (3DUI), Minneapolis, MN, pp. 75-82, 2014, doi: 10.1109/3DUI.2014.6798846, 8 pgs.

Gang Luo et al. "Registration of an on-axis see-through headmounted display and camera system" Optical Engineering, vol. 44(2) pp. 024002-7, Feb. 2005, 7 pgs.

International Preliminary Report on Patentability received for PCT Serial No. PCT/IL2021/050485, on May 11, 2023, 11 pgs.

International Search Report and Written Opinion received for PCT Serial No. PCT/IL2021/050485 on Aug. 8, 2021, 11 pgs.

* cited by examiner

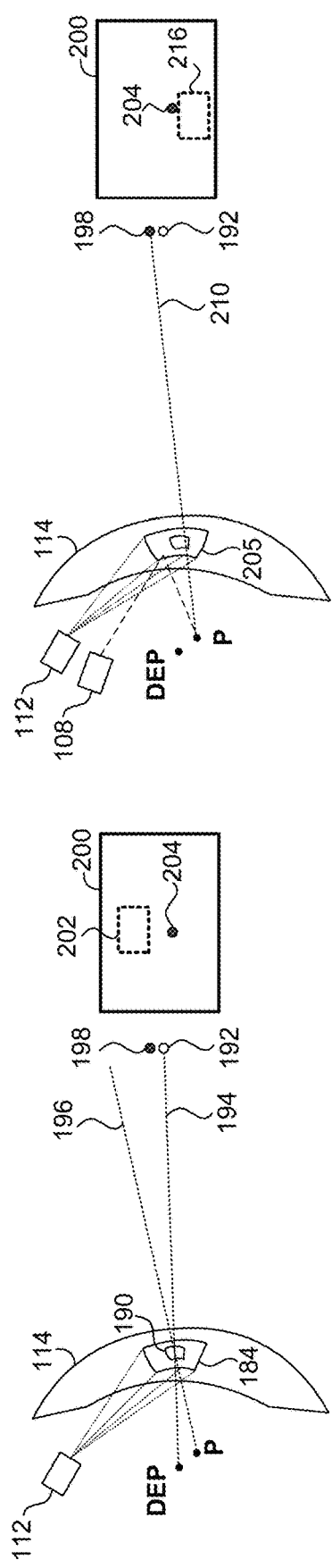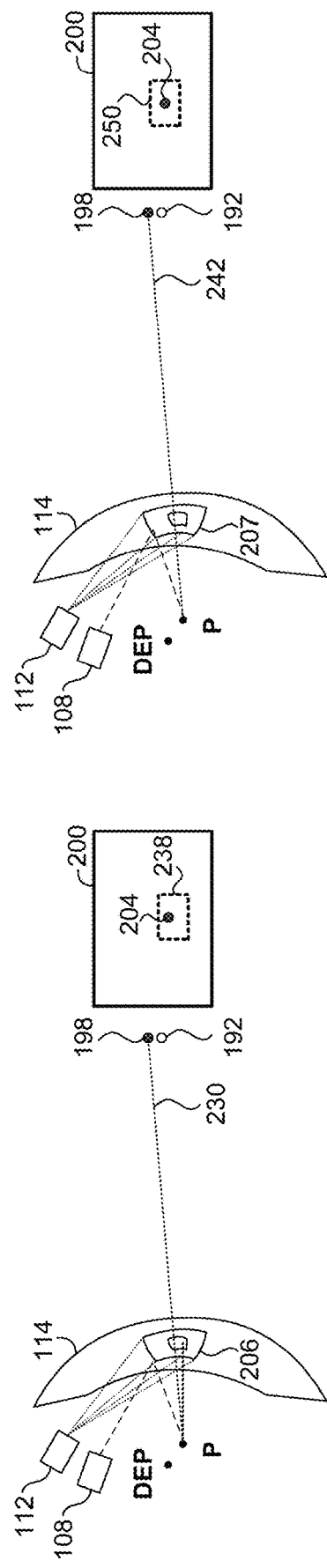

OPTICAL SEE THROUGH (OST) HEAD MOUNTED DISPLAY (HMD) SYSTEM AND METHOD FOR PRECISE ALIGNMENT OF VIRTUAL OBJECTS WITH OUTWARDLY VIEWED OBJECTS

CROSS-REFERENCE TO RELATED APPLICATIONS

The present application is a National Stage Filing of PCT International Application No. PCT/IL2021/050485 filed on Apr. 27, 2021, which is incorporated herein by reference in its entirety.

FIELD OF THE DISCLOSED TECHNIQUE

The disclosed technique relates to electro-optical systems and methods, in general, and to optical see-through (OST) head mounted display (HMD) systems and methods, in particular.

BACKGROUND OF THE DISCLOSED TECHNIQUE

An optical see-through (OST) head mounted display (HMD), in general is a wearable display device designed to be coupled with a head of a user that is capable of projecting images for viewing by the user while also permitting the user to see through at least part of it. A variety of OST HMD's are known in the art.

U.S. Patent Application Publication No.: US 2014/0078023 A1 to Ikeda et al. entitled "Display Device, Image Processing Device and Image Processing Method, and Computer Program" is directed to an image display system for correcting distortions of images caused by a state of a user, particularly when lens centers of eyepiece optical systems do not match the center positions of the eyes of the user. This mismatch causes at least part of a displayed image to appear distorted, or for each primary color R (red), G (green), B (blue) to appear shifted in at least part of a screen due to the magnification of chromatic aberrations of the lenses. The image display system includes a head-mount unit, a video reduction unit, a distortion correction unit, a correction vector retaining unit, a display unit, and an eyepiece optical system. The head-mount unit includes an eye interval adjusting mechanism, and independent display units for the left eye and the right eye of the user. Video reduction unit processes input video signals to be reduced so that the video signals are appropriate for the size of a display panel.

A distortion correction vector is created in advance according to an amount of shift between the lens centers of the eyepiece optical system and the center position of the eye of the user. Particularly, the distortion correction vector is used to correct magnified chromatic aberrations caused by mismatch of an interval that is smaller than a minimum unit correcting interval of the eye interval adjusting mechanism. The correction vector retaining unit stores the distortion correction vector that is created in advance. Eye interval adjusting mechanism adjusts a position of the display unit(s) with respect to the eye interval of a user in stages. After eye interval adjusting mechanism adjusts the eye interval as much as possible and the distortion correction unit corrects an image according to the correction vector, the distortion correction unit corrects distortion such that position adjustments smaller than the minimum unit correcting interval are interpolated. Particularly, the distortion correction unit corrects the displayed image based on the correction vector according to an amount of shift that remains after the eye interval adjusting mechanism performs the adjustment. The distortion correction unit thus functions to correct input images from the video reduction unit based on the correction vector according to mismatch of a lens center of the eyepiece optical system with the center position of an eye of the user.

U.S. Patent Application Publication No.: US 2011/0187844 A1 to Owaga et al. entitled "Image Irradiation System and Image Irradiation Method" is directed to an image irradiation system and method for generating and projecting images containing information toward a driver of a vehicle without requiring the driver to widely change his/her point of view. The image irradiation system includes a photographing device, a central processing module, a memory device, and an irradiation device. The photographing device includes a first camera and a second camera. The central processing module includes an image signal creation module, a first, second and third position calculation modules, an irradiation position decision module, a drive control module, and a distortion correction module. The photographing device, the irradiation device and the memory device are connected with the central processing module. The first camera is installed facing the driver for taking face photographs, while the second camera is installed above the driver for taking photographs of a head portion. The first position calculation module detects a single eye of the driver for every image inputted from the first camera. The first position calculation module calculates the position of the eye of the driver in a YZ surface perpendicular to the traveling direction of the vehicle. The irradiation position decision module decides a position at which the image is irradiated, based on the position of the eye. The drive control module outputs a control signal to a drive module such that the image is irradiated to an irradiation position determined by the irradiation position decision module.

The second position calculation module detects a center position of the head portion of the driver, as well as the position of the eye on the XY surface. The third position calculation module calculates the position of the eye of the user in an XYZ space based on the eye position on the YZ and XY surfaces, so as to input this position to the image signal creation module. The image creation module creates a projection image of fender poles at the position of the eye, based on corresponding relationship between the calculated eye position and position information of the fender poles. The memory device stores the positions of fender poles, which are installed on the leading edge of the vehicle. The created image signal is inputted to the distortion correction module. The distortion correction module corrects the image signal inputted from the image signal creation module based on the distortion correction information which is read from and stored in the memory device.

An article by Itoh, Y. and Klinker, G. entitled "Interaction-Free Calibration for Optical See-Through Head-Mounted Displays based on 3D Eye Localization" is directed at an interaction-free calibration method for OST-HMDs that utilizes three-dimensional (3-D) eye localization. The method utilizes 3-D eye position measurements acquired from an eye tracker in combination with pre-computed, static display calibration parameters. The eye tracker is rigidly attached to the bottom rim of an HMD, and is oriented towards one of the eyes of a user. A second camera determines the HMD pose within the surrounding world environment. An offline calibration process determines the rigid setup of the two cameras and the HMD. The HMD is mounted on the user's head. The method generates world-related augmentations in a moving HMD on the user's head, by combining static HMD calibration with dynamic eye tracking. The results of the study described in the article claim that the proposed calibration method with eye tracking is more stable than repeated single point active alignment method (SPAAM) calibrations.

SUMMARY OF THE PRESENT DISCLOSED TECHNIQUE

It is an object of the disclosed technique to provide a novel method and optical see-through (OST) head mounted display (HMD) system for providing precise alignment between a projected virtual object viewed by a user of an OST HMD and an optically see-through externally viewed object (e.g., real-world or virtual), such that the projected virtual object appears to the user superimposed in an aligned manner with respect to the external object that is either one of at least partially appearing outwardly and completely hidden to the user through the OST HMD. In accordance with the disclosed technique, there is thus provided an OST HMD system, for viewing an object associated with a first reference frame. The OST HMD system includes an electro-optical display module, and a processor. The electro-optical display module includes at least one partially reflective partially transmissive optical element, and at least one electro-optical projection module. The partially reflective partially transmissive optical element is configured for at least one of viewing therethrough the object, and viewing the image, by the user. The at least one electro-optical projection module is configured to irradiate the image for viewing by at least one eye of a user who wears the OST HMD. The electro-optical display module is associated with a second reference frame. The processor is configured to be coupled with the electro-optical display module. The processor is configured to generate the image, according to predetermined information, eyeball feature position data, and at least one of an orientation, and a position and orientation, so that the image appears to the user in an aligned manner with respect to the object. The eyeball feature position data is associated with at least one eyeball feature position of at least one eye of the user, with respect to the second reference frame. The at least one of orientation and position and orientation of the second reference frame is of the second reference frame with respect to the first reference frame. The predetermined information relates correction data of the OST HMD to a plurality of different respective position data values of at least one eyeball feature position. The object is either one of at least partially appearing outwardly and completely hidden to the user through the at least one partially reflective partially transmissive optical element when the image is irradiated by the at least one optical projection module.

According to accessorized implementations or configurations of the disclosed technique, the OST HMD system may further include a position determination module, a tracking system, and a memory device. The position determination module, the tracking system, and the memory device are configured to be communicatively coupled with the processor. The position determination module is configured to determine the at least one eyeball feature position of at least one eye with respect to the second reference frame, and to generate the corresponding eyeball feature position data. The tracking system is configured to determine the at least one orientation, and a position and orientation, of the second reference frame with respect to the first reference frame. The memory device is configured to store predetermined information relating correction data of the OST HMD to a plurality of different respective position data values of the at least one eyeball feature position.

In accordance with another aspect of the disclosed technique there is thus provided a method for irradiating an image in an OST HMD for viewing through the OST HMD an object associated with a first reference frame, by at least one eye of a user. The method includes generating and irradiating the image for viewing by the user, such that the image appears to the user superimposed in an aligned manner with respect to the object that is either one of at least partially appearing outwardly and completely hidden to the user, according to predetermined information, eyeball feature position data, and at least one of an orientation, and a position and orientation. The predetermined information relates correction data of the OST HMD with a plurality of different respective position data values of at least one eyeball feature position of the at least one eye. The eyeball feature position data is associated with at least one eyeball feature position of at least one eye, with respect to a second reference frame. The at least one of orientation and position and orientation is of the second reference frame with respect to the first reference frame. The object is either one of at least partially appearing outwardly and completely hidden to the user. The method may further include a procedure of generating the eyeball feature position data by determining corresponding at least one eyeball feature position. The method may further include a procedure of determining the at least one of an orientation, and a position and orientation, of the second reference frame with respect to the first reference frame.

BRIEF DESCRIPTION OF THE DRAWINGS

The disclosed technique will be understood and appreciated more fully from the following detailed description taken in conjunction with the drawings in which:

FIGS. 6A-6E show the fourth phase of the calibration procedure, and specifically:

FIG. 6A is a schematic illustration showing the effect of not correcting the eye position of a user, and OST aberrations, and electro-optical projection module and optical combiner aberrations;

FIG. 6B is a schematic illustration showing the effect of correcting the eye position of a user, but not correcting for OST aberrations, and electro-optical projection module and optical combiner aberrations;

FIG. 6C is a schematic illustration showing the effect of correcting for eye position of a user, and OST aberration correction, but not of correcting for electro-optical projection module and optical combiner aberrations;

FIG. 6D is a schematic illustration showing the effect of correcting for the eye position of a user, OST aberration correction, and electro-optical projection module and optical combiner aberrations;

FIG. 6E is a schematic block diagram illustrating a representation of the unified correction data in the form of a lookup table;

DETAILED DESCRIPTION OF THE EMBODIMENTS

Figure 1A:
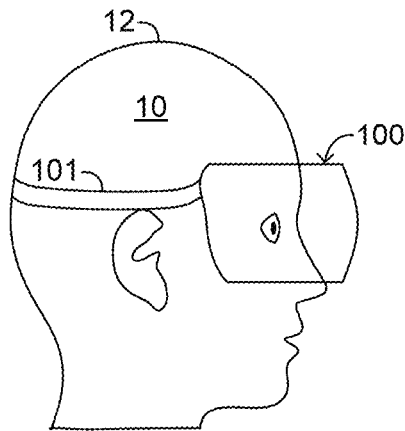
FIG. 1A is a schematic illustration of an optical see-through (OST) head mounted display (HMD) system, showing a particular mounting configuration on a user, constructed and operative in accordance with an embodiment of the disclosed technique.

The disclosed technique overcomes the disadvantages of the prior art by providing a method and optical see-through (OST) head mounted display (HMD) system that enable precise alignment between a projected virtual object viewed by a user of the OST HMD and an externally viewed object (e.g., real-world or virtual object such as the horizon, a virtual image, etc.), such that the projected virtual object appears to the user superimposed in an aligned manner with respect to the external object appearing outwardly to the user through the OST HMD. The OST displays of the disclosed technique may be based on technologies such as visor projection, combiners, waveguide techniques (e.g., microstructure extraction, diffractive optics or holograms, micromirror beam-splitters, polarization reflection techniques), retinal scanning, on-pupil optics or contact lenses, and the like. Among various types of HMDs, the disclosed technique involves HMDs that include at least an electro-optical display module, and a partially reflective partially transmissive optical element. A general overview of the system and method of the disclosed technique now follows.

In accordance with the disclosed technique, there is thus provided an OST HMD system, for viewing an object associated with a first reference frame. The OST HMD system includes an electro-optical display module, and a processor. The electro-optical display module includes at least one partially reflective partially transmissive optical element for viewing the object therethrough, and at least one electro-optical projection module configured to irradiate an image for viewing by at least one eye of a user who wears the OST HMD. The processor is configured to be coupled with the electro-optical display module. The processor is configured to generate the image, according to predetermined information, eyeball feature position data, and at least one of an orientation, and a position and orientation, so that the image appears to the user in an aligned manner with respect to the object. The eyeball feature position data is associated with at least one eyeball feature position of at least one eye of the user, with respect to the second reference frame. The at least one of orientation and position and orientation of the second reference frame is of the second reference frame with respect to the first reference frame. The predetermined information relates correction data of the OST HMD to a plurality of different respective position data values of at least one eyeball feature position. The object is either one of at least partially appearing outwardly and completely hidden to the user through the at least one partially reflective partially transmissive optical element when the image is irradiated by the at least one optical projection module.

According to accessorized implementations or configurations of the disclosed technique, the OST HMD system may further include a position determination module, a tracking system, and optionally a memory device. The position determination module is configured to determine the at least one eyeball feature position of at least one eye with respect to the second reference frame, and to generate the corresponding eyeball feature position data. According to one example implementation, the position determination module is an eye tracker integrated into the OST HMD system. The tracking system is configured to determine at least one of: (1) orientation, and (2) a position and orientation, of the second reference frame with respect to the first reference frame. The memory device is configured to store predetermined information relating correction data of the OST HMD to a plurality of different respective position data values of the at least one eyeball feature position.

In accordance with another aspect of the disclosed technique there is thus provided a method for irradiating an image in an OST HMD for viewing through the OST HMD an object associated with a first reference frame, by at least one eye of a user. The method includes a procedure of generating and irradiating the image for viewing by the user, such that the image appears to the user superimposed in an aligned manner with respect to the object that is either one of at least partially appearing outwardly and completely hidden to the user, according to predetermined information, eyeball feature position data, and at least one of an orientation, and a position and orientation. The predetermined information relates correction data of the OST HMD with a plurality of different respective position data values of at least one eyeball feature position of the at least one eye. The eyeball feature position data is associated with at least one eyeball feature position of at least one eye, with respect to a second reference frame. The at least one of orientation and position and orientation is of the second reference frame with respect to the first reference frame. The object is either one of at least partially appearing outwardly and completely hidden to the user. The method may further include a procedure of generating eyeball feature position data by determining corresponding at least one eyeball feature position. The method may further include a procedure of determining the at least one of an orientation, and a position and orientation, of the second reference frame with respect to the first reference frame. Without loss of generality, the at least one of orientation, and position and orientation is selected to be described herein from a perspective of the second reference frame with respect to the first reference frame, however, the reverse perspective wherein the at least one of orientation, and position and orientation of first reference frame is with respect to the second reference frame is likewise viable and applicable to the disclosed technique.

Figure 1B:
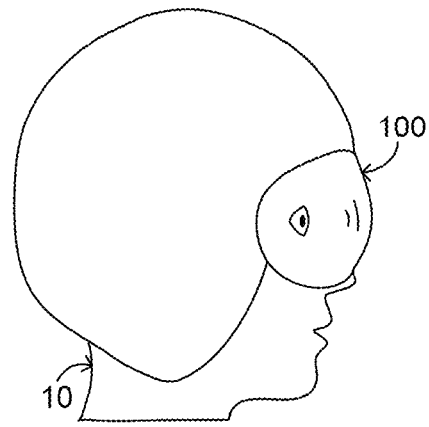
FIG. 1B is a schematic illustration of the OST HMD system, showing another mounting configuration on the user, constructed and operative in accordance with the embodiment of the disclosed technique.
Figure 2:
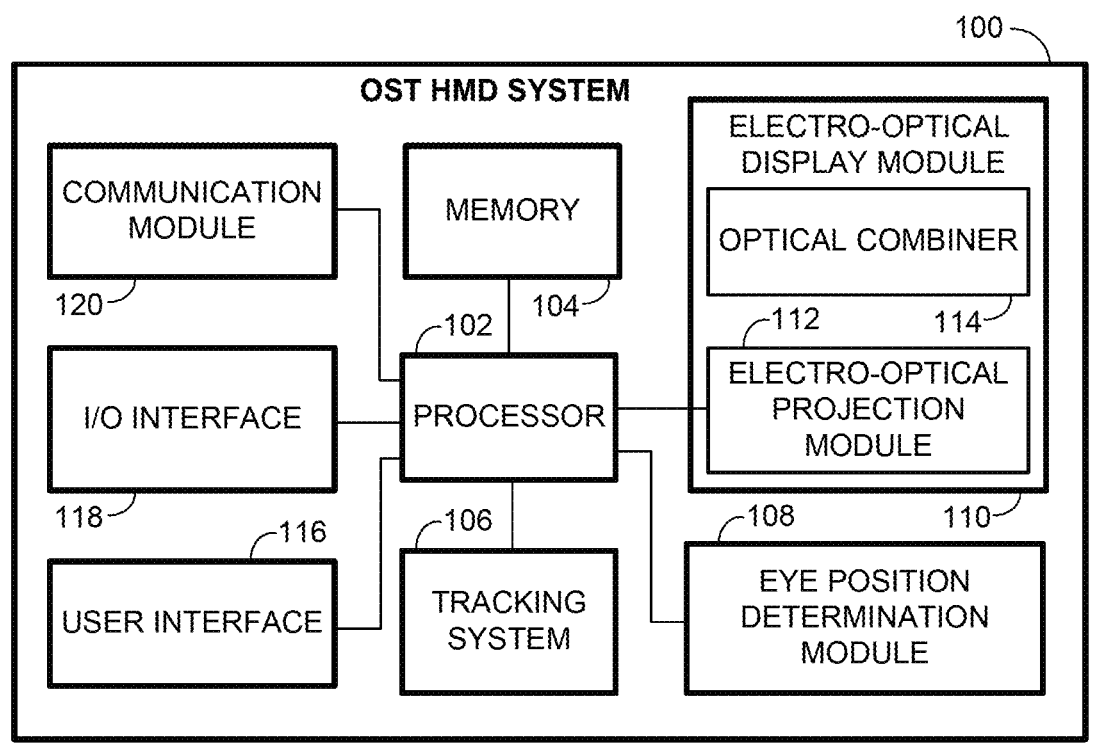
FIG. 2 is a top-level schematic block diagram of the OST HMD system, constructed and operative in accordance with the embodiment of the disclosed technique.

The following is a top-level description of the disclosed technique, which is followed by a more detailed, low-level description. Reference is now made to FIGS. 1A, 1B and 2. FIG. 1A is a schematic illustration of an optical see-through (OST) head mounted display (HMD) system, generally referenced 100, showing a particular mounting configuration on a user, constructed and operative in accordance with an embodiment of the disclosed technique. FIG. 1B is a schematic illustration of the OST HMD system, showing another mounting configuration on the user, constructed and operative in accordance with the embodiment of the disclosed technique. FIG. 2 is a top-level schematic block diagram of the OST HMD system, constructed and operative in accordance with the embodiment of the disclosed technique. FIG. 1A shows a general mounting configuration of OST HMD system 100 onto a head 12 of a user 10 utilizing at least one head coupler 101 (also referred interchangeably herein as "HMD-to-head coupler", helmet, or "harness"). Head coupler 101 is configured and operative to couple OST HMD system 100 firmly with at least a part of head 12 of user 10 so as to provide minimal movement between OST HMD system 100 and head 12, especially when head 12 moves. Head coupler 101 may typically be configured and constructed to be in the form of two longitudinal stems each extending from the two (i.e., right and left) sides of head 12. An alternative configuration and construction of head coupler 101 may take the form of a helmet as shown in FIG. 1B, configured to at least partially cover head 12 of user 10, as well as to provide protection to head 12 (i.e., from impact, injury, external environment, etc.). Other alternative configurations and constructions (not shown) of head coupler 101 include those utilizing a strap (e.g., a flexible adjustable strap) or straps (head and chip straps), a headband, overhead straps (e.g., having various configurations such extending longitudinally, crosswise, etc.), and the like.

With reference to FIG. 2, OST HMD system 100 is configured and operative to be implemented in four disparate and separate main configurations: (1) a basic configuration; (2) a first accessorized configuration; (3) a second accessorized configuration; and (4) a fully accessorized configuration. According to the basic configuration, OST HMD system 100 includes a processor 102, electro-optical display module 110, and optionally a memory device 104. The first accessorized configuration additionally includes (i.e., with respect to the basic configuration), a tracking system 106. The second accessorized configuration additionally includes (i.e., with respect to the basic configuration), an eye position determination module 108. The fully accessorized configuration includes all components of the basic configuration, the first accessorized configuration, the second accessorized configuration, as well as the following optional peripheral components: a user interface 116, an input/output (I/O) interface 118, and a communication module 120. Memory device 104 may optionally be included in each of the four aforementioned configurations (1)-(4). Optional peripheral components, namely, user interface 116, I/O interface 118, and communication module 120 may be included in each of aforementioned configurations (1)-(4). The first accessorized configuration (i.e., "configuration (2)") is denoted herein as "tracking-system-included, eye-position-determination-module-excluded configuration". The second accessorized configuration (i.e., configuration (3)") is denoted herein as "eye-position-determination-module-included, tracking-system-excluded configuration".

Electro-optical display module 110 includes an electro-optical projection module 112, and an optical combiner 114 (also referred interchangeably herein as "partially reflective partially transmissive optical element"). Processor 102 is configured to be coupled with the following components in accordance with the aforementioned configurations (1)-(4): memory device 104, tracking system 106, eye position determination module 108, electro-optical display module 110, user interface 116, I/O interface 118, and with communication module 120. Tracking system 106 may include a plurality of distinct units (e.g., 1061 (described in conjunction with FIG. 3), and the like). Tracking system 106, eye position determination module 108, and electro-optical projection module 112 collectively form what is hereinafter termed as the "optical assembly". (In the basic configuration, the optical assembly includes electro-optical projection module 112, but not tracking system 106, and eye position determination module 108.) The individual components of the optical assembly have fixed relative positions to each other (e.g., typically mechanically coupled to an enclosure or housing). For example, electro-optical display module 110 and eye position determination module 108 are mechanically coupled. The position and orientation of the optical assembly may assume various interchangeable arrangements (not shown) with respect to HMD-to-head coupler 101. During operation of OST HMD system 101 the optical assembly is mostly fixed with respect to HMD-to-head coupler 101.

As will be described in greater detail hereinbelow, according to the basic configuration, processor 102 is configured and operative to receive eyeball feature position data associated with at least one eyeball feature position of at least one eye of the user with respect to the second reference frame, as well as to receive at least one of the orientation and a position and orientation of the second reference frame with respect to the first reference frame. Alternatively, processor 102 possesses (e.g., is preprogrammed, has stored in internal memory, program, firmware thereof, etc.) at least one of the eyeball feature position data, and the at least one of the orientation, and position and orientation of the second reference frame with respect to the first reference frame.

Processor 102 is configured to receive the eyeball feature position data from a user (such as a technician measuring the eyeball feature position or from a known database/measurement) using user interface 118. Alternatively, processor 102 is configured to receive the eyeball feature position data via a communication module 116 (e.g., from the Internet, database, remote computer, technician, the user him/her/it-self, and the like). Further alternatively, processor 102 is configured to receive the eyeball feature position data from memory device 104. Further alternatively, processor 102 is configured to receive the eyeball feature position data from software, an algorithm, at least one medium capable of storing data and instructions executed by processor 102, and the like. Alternatively, processor 102 is configured and operative to receive the eyeball feature position data via an external eye position determination system (e.g., an eye-tracking system, such as an optical tracker, a contact lens type eye tracker, etc.) (not shown) that is not part of OST HMD system 100. The external eye position determination module is configured to generate the eyeball feature position data and provide it to OST HMD system 100 (e.g., to processor 102, to memory device 104). According to one implementation, the eyeball feature position data is provided during a calibration stage by projecting an image to a user to be aligned with a real-world object (e.g., a jig), whereby the user can repeatedly update the eyeball feature position data, which in turn processor 102 uses to generate the image, until it appears aligned with the object. Alternatively, the external eye position determination module and/or memory device 104 are configured to save eye position data inputted by the user to be retrieved by processor 102 for future use. Further alternatively, according to another implementation employing calibration for producing the eyeball feature position data, the calibration procedure produces a calibration set (not shown) of eyeball feature position data in which the user can indicate or select (i.e., input into OST HMD system 100) a user-preferred or user-selected eyeball feature position. It is noted, for example that the user-selected eyeball feature position may not necessarily be an actual eyeball feature position but rather an "effective eye position" for which OST HMD system 100 generates an aligned image when the user looks at a calibration jig (not shown) or calibration object (not shown). The eyeball feature position data can be user-selected based on a subjective view of the user, can be based on trial and error, as well as derived information and indirect measurement of the eyeball feature position itself (e.g., based on information pertaining to the position of at least one other body feature (e.g., nose contour) of the user and that latter body feature position in relation to the eyeball feature).

In the case of OST HMD system 100 receiving the eyeball feature position data from a calibration process, one implementation involves continuous use of OST HMD system 100 immediately after receiving eyeball feature position data from the calibration process (i.e., OST HMD system 100 is not shut down or turned off after receiving the eyeball feature position data). One option is that the calibration process for providing the eyeball feature position data is performed once when the OST HMD system 100 is turned on. Another option is that the calibration process is repeated at any time when there is a need to do so (e.g., there is a degradation of accuracy, such as when the HMD is shifted with respect to the head of the user). Alternatively, in case the HMD is positioned on the head of a user in a repetitive manner for the same user, memory device 104 is configured to store the user-specific calibration result (i.e., user-specific eyeball feature position data) such that it is associated with that user. Both alternatives may be useful for the same user of OST HMD system 100, for example when using OST HMD system 100 for visor-guided surgery (VGS). VGS is based on tracking and augmented reality. In VGS procedures performed with a VGS system, the HMD augments a surgeon's view of a patient thereby enabling the surgeon to view anatomical features (e.g., anatomical structures), surgical tools, implants, and other virtual objects as if the patient's body were partially transparent. Some of these procedures may require basic accuracy for which one-time calibration accuracy may be sufficient (i.e., even if the HMD is mounted on the head of the user in a slightly different position every time it is used). Other procedures may require very high accuracy and in those cases the user may perform calibration just prior to use of OST HMD system 100 without moving the HMD between calibration and use. An example for a VGS procedure that may require basic accuracy is a craniotomy, and an example for a VGS procedure that may require high accuracy is a biopsy of a small and deeply located brain tumor.

Further according to the basic configuration, processor 102 is configured and operative to receive the at least one of (1) orientation and (2) position and orientation, of the second reference frame with respect to the first reference frame via an external tracking system (not shown) that is not part of OST HMD system 100. Such a tracking system may be installed at an area, site, and space, where the user is located or intended to be located (e.g., a vehicle such as a cockpit of an aircraft, part of a building, an outdoor area, etc.). Optionally, at least part of such a tracking system (e.g., active and/or passive markers, sensors, and the like) is located on the OST HMD. Example tracking systems include optical tracking systems and methods employing optical detectors (e.g., cameras) that employ computer vision algorithms, electromagnetic (EM) tracking systems and methods employing EM field generation and corresponding EM sensors.

The first accessorized configuration additionally includes (with respect to the basic configuration), tracking system 106, which will be elaborated on hereinbelow. Furthermore, tracking system 106, which is an integral part of the first accessorized configuration, can be implemented by the example techniques specified above (e.g., optical tracking, EM tracking, computer vision algorithms, and the like).

The second accessorized configuration further includes (with respect to the basic configuration), eye position determination module 108, which will be elaborated on hereinbelow. Furthermore, eye position determination module 108 can be implemented by the techniques specified above. According to one implementation, eye position determination module 108 is configured to output eyeball feature position data from time to time (e.g., a scheduled manner, when there's a requirement due to changing conditions and/or users, etc.). Alternatively, eye position determination module 108 is configured to output eyeball feature position data continuously (e.g., in real-time using a real-time eye-tracker).

In the following description, any mentioned component with its corresponding function is associated with a configuration (i.e., among (1)-(4)) that includes that component. For example, an embodiment that includes a tracking system is applicable to the first accessorized configuration (2). An embodiment that includes an eye position determination module is applicable to the second accessorized configuration (3). An embodiment that includes both tracking system and eye position determination module is applicable to the fully accessorized configuration (4). An embodiment that excludes both tracking system and eye position determination module is applicable to the basic configuration (1).

Figure 3:
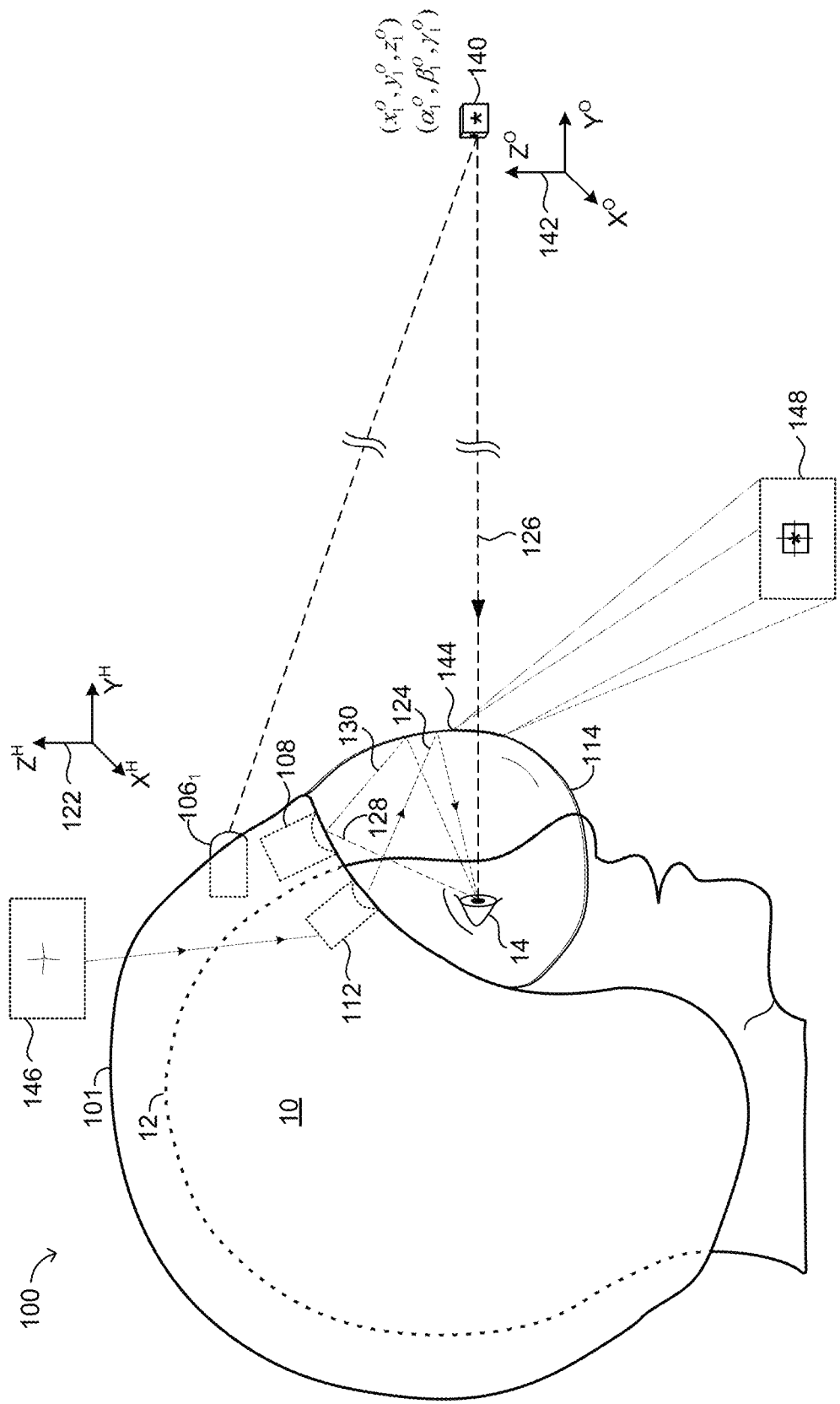
FIG. 3 is a schematic illustration showing high-level configuration and operation aspects of the OST HMD system, constructed and operative in accordance with the embodiment of the disclosed technique.

Reference is now further made to FIG. 3, which is a schematic illustration showing high-level configuration and operation aspects of the OST HMD system, constructed and operative in accordance with the embodiment of the disclosed technique. FIG. 3 illustrates OST HMD system 100 mounted onto user 10 via HMD-to-user coupler 101 that assumes a general form of a helmet (i.e., referred herein interchangeably, and without loss of generality as "helmet 101"). OST HMD system 100 enables user 10 to view an object 140 that is located at a distance from user 10 and appears to the user outwardly through partially reflective partially transmissive optical element 114. OST HMD system 100 is associated with an optical assembly reference frame 122 (also denoted interchangeably herein as "HMD reference frame 122"), shown representatively in FIG. 3 as a 3-dimensional (3-D) Cartesian coordinate system whose axes are denoted by convention $(X^H, Y^H, Z^H)$, where the 'H' superscript signifies HMD for brevity. Analogously, object 140 is associated with an object reference frame 142, shown representatively in FIG. 3 as a 3-D Cartesian coordinate system whose axes are denoted by convention $(X^O, Y^O, Z^O)$, where the 'O' superscript signifies, and is brevity for, 'Object'. Object 140 may have at least one of a known position and a known orientation with respect to object reference frame 142, indicated generally by $(x^O, y^O, z^O)$ denoting position and $(\alpha^O, \beta^O, \gamma^O)$ denoting orientation (e.g., via Euler angles, axis-angle representation, etc.). An example for object 140 having only a known position is a point-like object (e.g., point light source). An example for object 140 having only a known orientation is the horizon (in which case the object coordinate system can be chosen arbitrarily, for example Earth's coordinate (longitude, latitude, altitude)). Preferably (but without loss of generality in the selection of a coordinate system), the system and method of the disclosed technique employ (for applications involving piloting of aircraft) a local-level, local-north (LLLN) coordinate system (also known in the art as a north-east-down (NED) coordinate system, also known as local tangent plane (LTP) coordinate system). Particular positions and orientations are denoted herein by subscripts. For example, a particular position (e.g., position '1') of object 140 in object reference frame 142 is denoted by $(x_1^O, y_1^O, z_1^O)$, and a particular orientation (e.g., orientation '1') of the object is denoted by $(\alpha_1^O, \beta_1^O, \gamma_1^O)$. Without loss of generality, the 3-D Cartesian coordinate system is chosen as a basis for describing the principles disclosed technique, however, it is noted that alternative coordinate systems, conventions, and formalisms may be used to indicate position and describe particulars of the disclosed technique, for example, generalized coordinates and the like.

FIG. 3 further shows the optical assembly including at least a part of tracking system 106 (a tracking system unit denoted by 106₁), eye position determination module 108, and electro-optical projection module 112 being arranged in fixed relative positions and orientations with respect to helmet 101, according to one example arrangement. According to one (simple) implementation, the position of the optical assembly is known with respect to eye 14 of user 10. According to another (typical) implementation, the position of the optical assembly with respect to eye 14 is not known a priori. In such a case it may be advantageous to define a particular point in optical assembly reference frame 122 as the "nominal eye position" (or design eye position (DEP)) which is an approximate position of an average eye.

Electro-optical projection module 112 is configured and operative to irradiate and to project light encoded with information (e.g., an image) for viewing by at least one eye 14 of user 10 wearing OST HMD system 100 (as shown in FIG. 1). Specifically, electro-optical projection module 112 emits light beams that are typically encoded with information, diagrammatically represented by a light ray 124 (FIG. 3), that impinge and at least partially reflect from partially reflective partially transmissive optical element 114 toward eye 14 of user 10. Partially transmissive partially reflective optical element 114 is configured and operative to allow the irradiated light to at least partially reflect off its surface toward at least one eye 14 of user 10, while also concurrently allowing at least partial transmission therethrough of incoming light from the surrounding or forward-facing physical environment viewed by the user (diagrammatically represented by incoming light ray 126). In effect, partially transmissive partially reflective optical element 114 is configured and operative as an optical combiner that enables the irradiated light encoded with information (e.g., a virtual object) to be superimposed (overlaid) over a viewed scene of the physical environment, the particulars of which will be described hereinbelow. The irradiated light encoded with information is typically an image 144 that is formed and is reflected off partially reflective surface of partially transmissive partially reflective optical element 114. In general, partially transmissive partially reflective optical element 114 (i.e., "optical combiner 114" for brevity) is typically composed of a combination of sub-elements that include a strong, durable, impact-resistant primary material (e.g., polycarbonate), that is substantially optically transparent (e.g., in the visible part of the EM spectrum), as well as one or plurality of thin film reflection coating(s), etc. Electro-optical projection module 112 may be embodied in the form of a micro-display, a near-eye display, and the like.

Eye position determination module 108 is configured and operative to determine at least one eyeball feature position associated with at least one eyeball feature position of eye 14 of user 10 wearing OST HMD 100, and to generate corresponding eyeball feature position data. The term "eyeball feature" refers herein to any detectable (e.g., optically) feature of the eyeball of the user, such as the pupil, iris, blood vessels, limbus, etc. The term "eyeball feature position" refers herein to at least a partial position (e.g., a 2-D position without depth) of an eyeball feature with respect to a reference frame. Alternatively, an eyeball feature position of a corresponding eyeball feature can include 3-D feature position information. The term "eyeball feature position data" refers to data pertaining to eyeball feature position (e.g., 2-D eyeball feature position data, 3-D eyeball feature position data, a location of an eyeball feature present in an image of at least part of the eyeball), or derivative data (e.g., indirect measurement data) pertaining to the position of the eyeball feature or data that can be used to derive the eyeball feature position data (e.g., via a mathematical relation). It is noted that according to one implementation, the exact knowledge of the eyeball feature position within reference frame 122 is not necessary. For example, eye position determination module 108 determines eyeball feature position data in an acquired image of the eyeball feature that is associated with the eyeball feature position (not determined). The disclosed technique is configured and operative to associate the determined eyeball feature position data with respective correction data. Eye position determination module 108 is further configured and operative to provide (e.g., transmit) the eyeball feature position data to processor 102 (FIG. 2). In accordance with one configuration, eye position determination module 108 includes hardware (e.g., an internal processor) that is configured to determine eyeball feature position data and generate corresponding eyeball feature position data. In accordance with another configuration, eye position determination module 108 detects eyeball features and provides data (e.g., raw, unprocessed) pertaining to those detected features to processor 102, which in turn determines at least one eyeball feature position from data received from eye position determination module 108. According to one implementation, eye position determination module 108 includes at least one camera configured to acquire at least one image of at least one eyeball feature. According to other implementations, eye position determination module 108 includes at least one optical sensor (e.g., a photo-detector), a combination of optical sensors and light sources (e.g., infrared (IR) light emitting diodes (LEDs), light beam scanning devices (e.g., incorporating microelectromechanical systems (MEMS) and lasers), and the like. Eye position determination module 108 may include several components integrated into one unit. Alternatively, eye position determination module 108 may include several components separated apart (e.g., an optical sensor located at a distance from a light source such as an IR LED). According to another implementation, there are multiple eye position determination modules, the specifics of which will be described in greater detail hereinbelow in conjunction with FIGS. 12A and 12B.

Memory device 104 (FIG. 2) is configured and operative to store predetermined information relating correction data of OST HMD (including electro-optical display module 110 that includes optical combiner 114 (having particular optical characteristics) and electro-optical projection module 112) to a plurality of different respective position data values of corresponding at least one eyeball feature position. Memory device 104 enables retrieval of the predetermined information stored therein. Specifically, memory device 104 stores predetermined information that associates correction data (e.g., generated by a calibration method) of optical combiner 114 and electro-optical display module 110 with a plurality of different respective position data values of corresponding at least one eyeball feature position of eye 14 of user 10 (i.e., this association as well as the calibration method are described in detail hereinbelow in the low-level description of the disclosed technique). A non-limiting example of a preferred eyeball feature position is a center position of a pupil of eye 14. Alternatively, memory device 104 is embodied in at least one implementation that includes being a part of an internal memory of processor 102 (FIG. 2), firmware of processor 102, and software configured to be run by processor 102. Further alternatively, memory device 104 is located away and separate from processor 102 (e.g., an external storage database such as in the cloud, an external data storage device(s), an external computer, a computer network, and the like). For example, memory device 104 can be incorporated into the electronics of a user's HMD (e.g., pilot's helmet) that is enabled to store calibration data, (e.g., predetermined information), user-specific calibration data, manufacturing data, etc., as well as to connect to OST HMD 100 (e.g., during calibration, initialization, routine function, etc.). Alternatively, processor 102 is installed the electronics of a vehicle such as an aircraft and memory device 104 incorporated into the user's HMD (e.g., pilot's helmet). According to this alternative, once there's an established a connection between the pilot's HMD and the aircraft's electronics, the processor in the aircraft (e.g., during initialization, re-calibration, etc.) reads the calibration data from the HMD. Processor 102 (whether installed in at least one of the aircraft, and the HMD), is configured to store the user-specific calibration data (e.g., for each vehicle operator such as pilot, driver, etc.), that is associated with that user (e.g., identifiable via the manufacturing data such as the HMD's serial number). Note that processor 102 may include of a plurality of processing sub-units (not shown), integrated together. Alternatively the plurality of processing sub-units may be located away from each other (not shown) (e.g., part of processor 102, e.g., at least one processing sub-unit is located in user's HMD, and at least one other processing sub-unit is located in a vehicle operated by that user (e.g., aircraft, land vehicle, sea vessel, etc.). Further note that memory device 104 may include a plurality of memory sub-units (not shown), which can be integrated together. Alternatively, at least part of the memory sub-units is located away from each other (not shown).

The term "optical characteristic" referenced herein either in singular or in plural, ascribed or pertaining to a particular object, refers to any attribute, quality, trait, property and phenomenon in the science of optics that optically defines, influences, characterizes, determines, describes, and is associated with that object. Example optical characteristics of optical combiner 114, include the diopter, refractive index, curvature, Abbe number, power error(s), optical element (e.g., lens) induced astigmatism, transmission coefficient, reflection coefficient, spectral (e.g., ultraviolet) cutoff wavelength, spectral transmission and reflection profile, lens dimensions (e.g., thickness), lens color (e.g., color-tinted), etc.

Tracking system 106 (FIG. 2) is configured and operative to determine at least one of: (1) a position, and (2) an orientation, i.e., position or orientation, or both position and orientation, denoted interchangeably as "position and/or orientation" of optical assembly reference frame 122 with respect to object reference frame 142 (FIG. 3). At least one of tracking system 106 and processor 102 is configured to determine (e.g., calculate) the position and/or orientation. Alternatively, at least one of tracking system 106, memory device 104, and processor 102 is configured to store the position and/or orientation. Alternatively, tracking system 106 may determine position and/or orientation of object 140 with respect to optical assembly reference frame 122. Hence, tracking system 106 determines the position and/or orientation of head 12 of user 10 wearing helmet 101 with respect to the position $(x_1°, y_1°, z_1°)$ and orientation $(\alpha_1°, \beta_1°, \gamma_1°)$ of object 140. For example, if user 10 is piloting an aircraft and object 140 is Earth, the orientation $(\alpha_1°, \beta_1°, \gamma_1°)$ of head 12 of user 10 with respect to object reference frame 142 may be used to display to the user a horizon line such that it is superimposed on Earth's horizon. The respective positions and/or orientations between tracking system unit $106_1$ and other helmet-mounted components of system 100, such as eye position determination module 108, electro-optical projection module 112, and optical combiner 114, may be known (e.g., via a calibration procedure), given the rigid relative spatial relationship therebetween. In a calibration procedure the positions and/or orientations of eye position determination module 108, electro-optical projection module 112, and optical combiner 114 in HMD reference frame 122 may be determined. In the case OST HMD 100 has a substantially collimated optical design, the projected image is theoretically at infinity and the knowledge of the position of electro-optical projection module 112 is not required. In various implementations the position and orientation of eye position determination module 108 is also not required (i.e. in order to generate eyeball feature position data). For example, in various implementations (such as pilot applications) only the orientation of tracking system unit $106_1$ relative to electro-optical projection module 112 is required. In other implementations (such as medical applications) there is a need to also perform calibration between tracking system unit $106_1$ and eye position determination module 108. Tracking system 106 typically employs optical methods such as at least one camera (e.g., a stereo camera, two cameras, 3-D optical sensor that generates a 2-D image and an additional depth image), optical projection and photogrammetric methods, electromagnetic (EM) methods, inertial measurement methods, global position system (GPS) methods, and the like. For example, tracking system 106 may be configured as an outside-in optical tracker employing passive optical reflectors on the helmet and sensors in the object reference frame, an inside-out optical tracker employing sensors on the helmet and light sources (e.g., light-emitting-diodes (LEDs)) in the object reference frame, or a combination thereof (e.g., an opto-inertial in-out/out-in tracker). Alternatively, tracking system 106 may be configured and operative as an electromagnetic field tracker in which for example tracking system unit $106_1$ (denoted interchangeably herein "tracker unit") senses the EM field generated by a transmitter located in object reference frame 142 and provides the sensed readings to processor 102 via I/O interface 118 and/or communication module 120. Tracking system 106 provides the determined position and/or orientation of optical assembly reference frame 122 with respect to object reference frame 142, to processor 102.

Processor 102 is configured and operative to generate and provide an image 146 (image data) to electro-optical projection module 112, based on the output from tracking system 106, the predetermined information stored in memory device 104, and eyeball feature position data, so that (irradiated and projected) image 144 appears to user 10 in an aligned manner with respect to object 140 located outwardly from the user through optical combiner 114, representatively illustrated in FIG. 3 by a superimposed image 148. Image 146 has been pre-distorted or corrected by processor 102 such that when electro-optical projection module 112 irradiates and projects (irradiated, projected and then partially reflected) image 144 onto optical combiner 114 it is seen aligned with respect to object 140 by user 10. The terms "aligned", and "alignment" refer herein to arriving at or being at least one of: matched relative position, matched relative orientation, and matched size (scaling) between an image and a real-world object. For example, an aligned arrangement is an image of a point indicating a location in an object within a body, such as a center of a tumor in the brain (i.e., aligned center-position), an image of a line indicating a horizontal level with respect to a linear object (i.e., aligned orientation), an image of a line indicating the true horizon to an aircraft pilot user (i.e., aligned position and orientation), an image of a symbol indicating the direction to a target foe aircraft for a pilot (i.e., aligned position), an image of a line indicating a proposed contour of an incision to be made inside or outside the body of a patient (i.e., aligned position, orientation, and scaling), or guidance trajectory of a tool to be inserted to a body (i.e., aligned position and orientation), an image of contours of structures (e.g., buildings, mountains, landmarks, etc. that may be completely or partially hidden to a pilot (e.g., due to fog, or other low visibility conditions (e.g., at night), precisely aligned and superimposed on the real-world structures (i.e., aligned position, orientation, and scaling). In the last example OST HMD system 100 enables to assist a pilot in avoiding collision with these structures. Further examples in the medical realm include a 3-D image segmentation of a body part or tissue constructed and/or rendered from medical imagery (e.g. of a tumor in a brain constructed and/or rendered from magnetic resonance imaging (MRI), a vertebra constructed and/or rendered from a computerized tomography (CT) scan), superimposed precisely on a real-world body part or tissue within the body that is hidden to the user when viewed directly. Further examples include a combination of synthetic 3-D objects to be displayed to the user where image data of 3-D objects are derived from different sources, for example image data of a tumor derived from an MRI scan, image data of a skull derived from a CT scan, a tool or implant model derived from 3-D computer-aided design (CAD) (3-D known model), and the like. Processor 102 is optionally further configured to determine the distance (alternatively, receive distance information) between the second reference frame and the real-world object so as to further scale (i.e., determine or adjust the dimensions of) image 146 to correspond with said distance.

Another example is a projected synthetic image superimposed onto a real-world scene containing a hidden object not directly seen by user 10, such as in a minimally invasive surgery setting, where the hidden object is an internal body part, and the external projected synthetic image is aligned (i.e., overlaid onto corresponding position) with that body part. This implementation of the disclosed technique will be further elaborated hereinbelow in conjunction with FIGS. 13A and 13B. FIG. 3 illustrates an alignment between real-world object 140 as seen by user and image 146 that is irradiated, projected and formed on optical combiner 114 as image 144 such that crosshairs of image 146 are matched in terms of position and orientation with respect to position and orientation of object 140, depicted as a superimposed image 148. As will be elucidated in a low-level description of the disclosed technique, which follows, alignment is achieved by taking into consideration the following: the position and orientation of the optical assembly with respect to the position and orientation of object 140, the position of the eye of the user ("eye location") with respect to the optical assembly, as well as see-through errors depending on eye location such as prismatic effect, aberration (e.g., distortion) effects of partially reflective partially transmissive optical element (e.g., due to its curvature, and other optical characteristics), as well as distortion effects arising from the electro-optical projection module.

Figure 4:
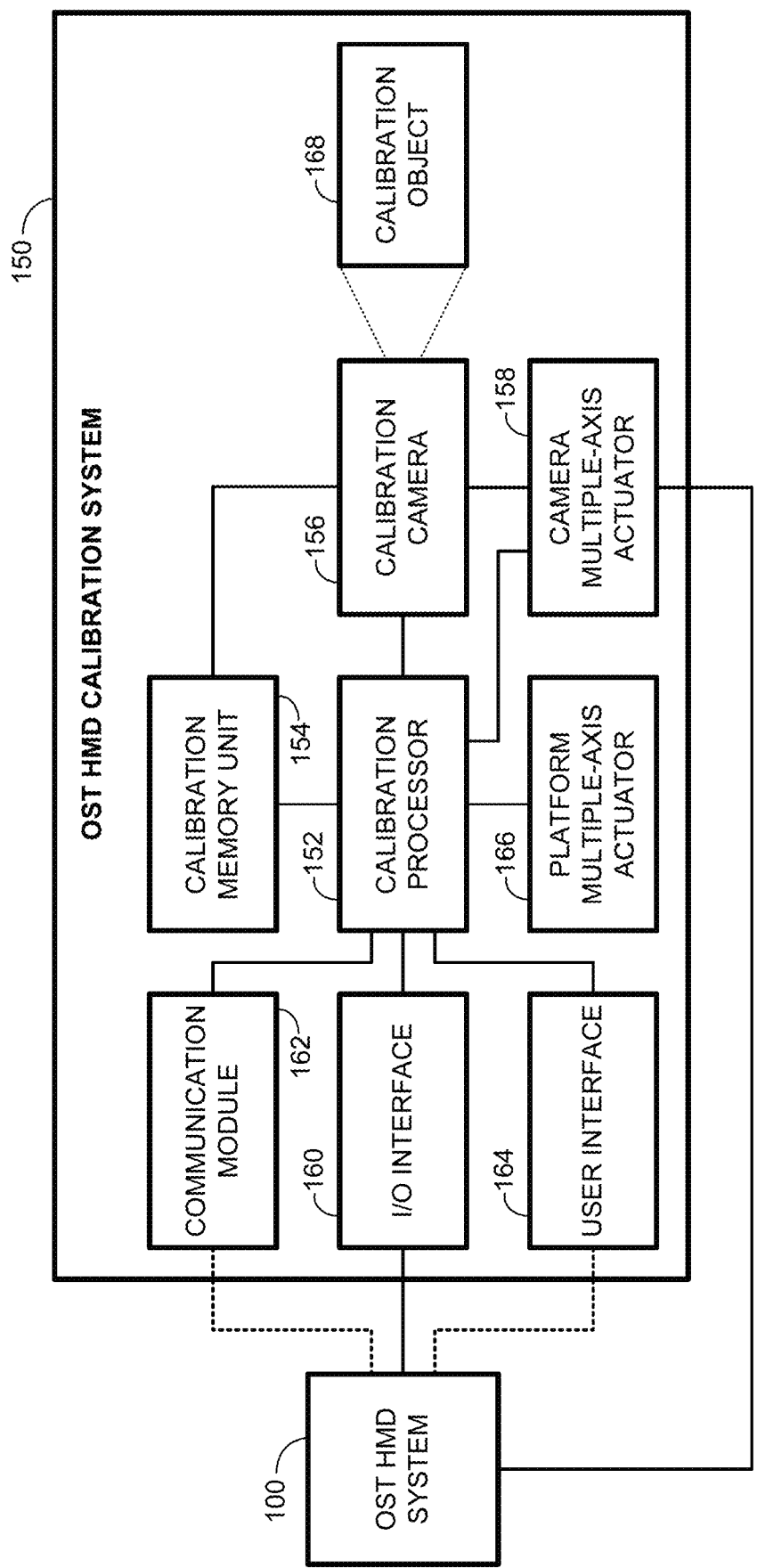
FIG. 4 is a schematic block diagram of an OST HMD calibration system, associated with OST HMD system of FIG. 2, constructed and operative in accordance with the embodiment of the disclosed technique.

A low-level description of the disclosed technique now follows. To achieve alignment, an initial calibration procedure (method) of OST HMD system 100 is performed by a calibration system. Reference is now made to FIG. 4, which is a schematic block diagram of an OST HMD calibration system, generally referenced 150, associated with OST HMD system 100 of FIG. 2, constructed and operative in accordance with the embodiment of the disclosed technique. OST HMD calibration system 150 includes a calibration processor 152, a calibration memory unit 154, a calibration camera 156, a (calibration) camera multiple-axis actuator 158, a calibration input/output (I/O) interface 160, a calibration communication module 162, a calibration user interface 164, and an optional platform multiple-axis actuator 166. Calibration processor 152 is coupled with calibration memory unit 154, calibration camera 156, camera multiple-axis actuator 158, calibration I/O interface 160, calibration communication module 162, calibration user interface 164, and with platform multiple-axis actuator 166. Calibration memory unit 154 may be further coupled with calibration camera 156 (further configured and operative as a data buffer). Camera multiple-axis actuator 158 is further mechanically coupled with calibration camera 156. Platform multiple-axis actuator 166 is further mechanically coupled with at least part of OST HMD calibration system 150, and helmet 101. OST HMD calibration system 150 is coupled with OST HMD system 100 (FIG. 2) via I/O interface 160. Alternatively or additionally, OST HMD calibration system 150 is coupled with OST HMD system 100 via communication module 162. Further alternatively or further additionally, OST HMD calibration system 150 is coupled with OST HMD system 100 via user interface 164.

Calibration processor 152 is configured and operative to process data pertaining to the calibration procedure, as will be described hereinbelow in greater detail. The example calibration procedure that is described hereinbelow is an example given to elucidate the general principles of the disclosed technique. Other example calibration procedures may be applicable with the disclosed technique. Generally, calibration camera 156 is configured and operative to acquire at least one image of a calibration object 168 (i.e., physical or synthetic (e.g., projected image)) that is separated by a certain distance from calibration camera 156. It is noted that the calibration procedure described for the purposes of elucidating the principles of the disclosed technique may not require a calibration object (e.g., such as in a calibration method that employs calibration camera pairs, i.e., two cameras directed at one another). The relative position and orientation of calibration object 168 with respect to the position and orientation of calibration camera 156 may be known (i.e., determined, measured). Calibration memory unit 154 is configured and operative to store data pertaining to the calibration procedure for retrieval. Camera multiple-axis actuator 158 is configured and operative to mechanically move calibration camera 156 to specific positions (i.e., in three spatial axes (X, Y, Z)) with respect to HMD reference frame 122. By controlling camera multiple-axis actuator 158, calibration processor 152 controls the position of calibration camera 156 in HMD reference frame 122. An additional tracker unit (not shown), similar to 106₁ (FIG. 3), may be attached to calibration camera 156, such that tracking system 106 may be configured to use this additional tracker unit to determine an exact position of calibration camera 156 in HMD reference frame 122 during each stage of the calibration procedure. I/O interface 160 is configured and operative to couple with I/O interface 118 (FIG. 2) of OST HMD system 100. Communication module 162 is configured and operative to communicate data at least with OST HMD system 100 (e.g., via communication module 120). User interface 164 is configured and operative to interact with a user (not shown), specifically, to receive user input as well as to provide output (e.g., via a monitor (not shown)).

Now the example calibration procedure will be described in conjunction with FIGS. 5A, 5B, 5C, 6A, 6B, 6C, 6D, and 6E. Without loss of generality, the example calibration procedure is the preferred (default) calibration procedure of the disclosed technique. To further detail the various phases of the calibration procedure, reference is now further made to FIG. 5A, which is a schematic diagram showing a first phase in a calibration procedure of OST HMD system, constructed and operative in accordance with the embodiment of the disclosed technique. The initial phase in the example calibration procedure involves mounting OST HMD system 100 including calibration camera 156, and calibration object 168 securely on at least one platform (e.g., two platforms 170₁ and 170₂ are shown in FIG. 5A) such that calibration camera 156 has a direct line-of-sight (LOS) to calibration object 168, without partially reflective partially transmissive optical element 114 (provisionally removed) being interposed therebetween.

Figure 5A:
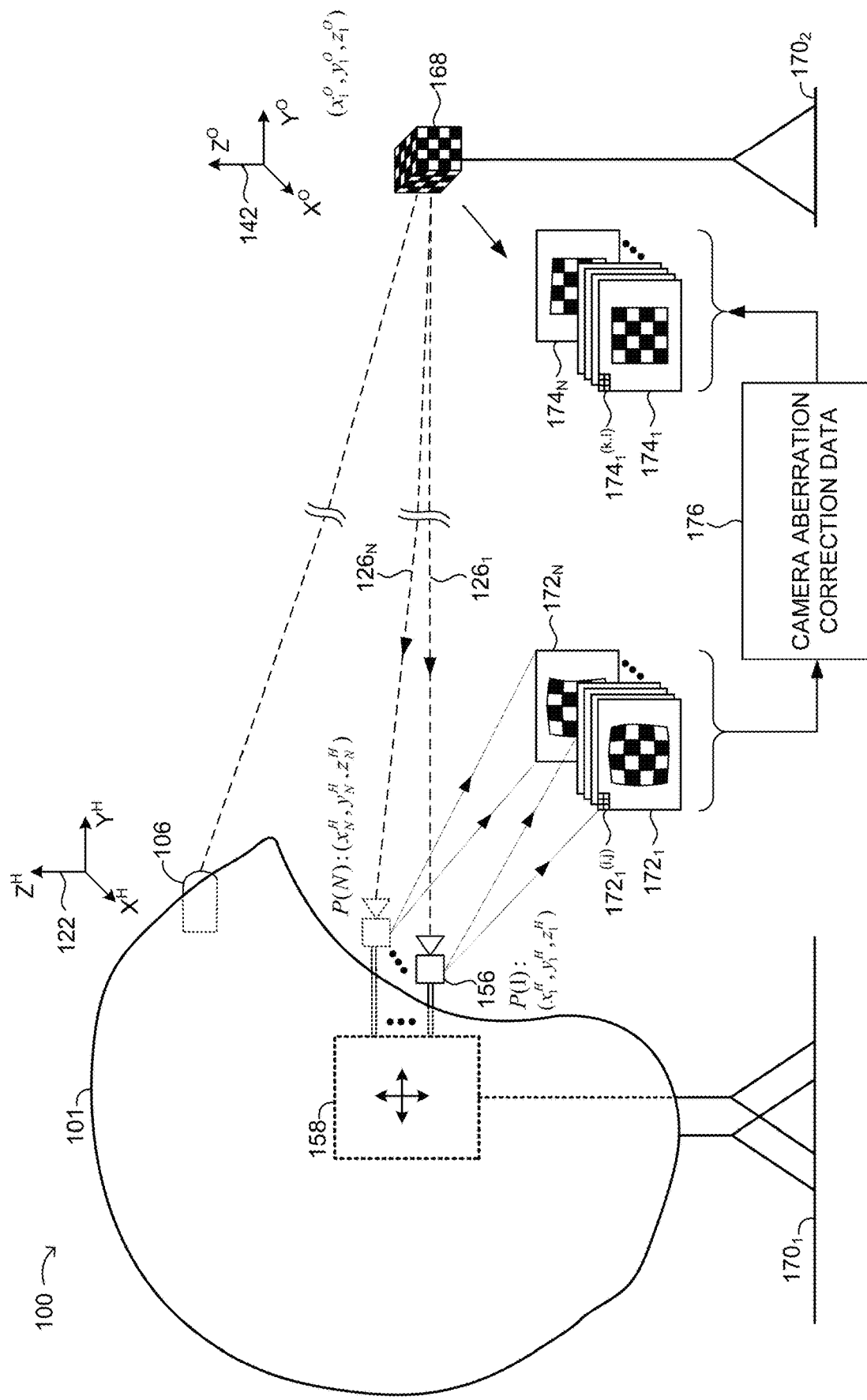
FIG. 5A is a schematic diagram showing a first phase in a calibration procedure of OST HMD system, constructed and operative in accordance with the embodiment of the disclosed technique.

The first phase of the calibration procedure determines a camera aberration correction data (reference data) 176, which pertains to various parameters that associate an image of a distant object acquired by a calibration camera in at least one camera position and orientation but without loss of generality FIG. 5A shows different camera positions (and orientations—not shown) in which the optical combiner has been removed from the line of sight (i.e., between calibration camera and calibration object). Alternatively, it is assumed that calibration camera 156 is pre-calibrated and its calibration parameters relating to aberrations (including distortions) are known. One possibility for storing and saving a representation of the calibration parameters is through a camera calibration look-up table. Both calibration memory unit 154 (FIG. 4) and memory device 104 (FIG. 2) separately and individually are configured and operative to store the camera calibration look-up table of the calibration parameters. Alternatively, processor 102 (FIG. 2) is configured to run code that includes the calibration look-up table of the calibration parameters. In such an implementation the memory (e.g., memory device 104, memory unit 154) is embodied in the form of computer code (not shown). In such a look-up table, for example, one column may include a list of all the pixels of the calibration camera's sensor, and second and third columns may include data describing a shift (e.g., corresponding to the dimension of the pixels) in the x-direction and y-direction respectively, that is required to generate a distortion-free image from a raw image (produced by the sensor). In general, the shift is not necessarily an integer number of pixels, and this description is just one, specific and simplistic example of distortion correction parameterization. It is also typically assumed that the dimensions of calibration object 168 are large enough so that its angular size, as captured by calibration camera 156, is at least as the dimensions of an image displayed on optical combiner 114 (currently removed in FIG. 5A). Alternatively, calibration camera 156 is distortion-free (i.e., not requiring the calibration look-up table).

Calibration camera 156 is configured and operative to capture a plurality of calibration images $172_1, \ldots, 172_N$ (where index N is a positive integer) of calibration object 168 from at least one position, and generally for N different positions denoted respectively as P(1), . . . , P(N) in HMD reference frame 122. Specifically, calibration camera 156 captures a calibration image $172_1$ of object 168 at position $(x_1^H, y_1^H, z_1^H)$, a calibration image $172_2$ of object 168 at position ($x_2^H$, $y_2^H$, $z_2^H$), and so forth to N, namely, a calibration image $172_N$ of object 168 at position ($x_N^H$, $y_N^H$, $z_N^H$). Camera multiple-axis actuator 158 is configured and operative to spatially move calibration camera 156 (e.g., via electric motors) to N positions P(1) through P(N), as diagrammatically illustrated in FIG. 5A. Calibration memory unit 154 is configured and operative to store calibration images $172_1$, . . . , $172_N$. The various positions from which calibration camera 156 acquires plurality of calibration images $172_1$, . . . , $172_N$ represent various typical eye positions of eye 14 of a user wearing helmet 101.

For each calibration image $172_1$, . . . , $172_N$ captured, there corresponds a respective camera aberration-free image $174_1$, . . . , $174_N$ of calibration object 168 that is without camera optical aberration. Calibration object 168 acts as a standard, typically embodied in the form of a printed pattern of known design, geometry, dimensions, mathematical description, etc. Alternatively, calibration object 168 is embodied as a displayed (virtual) object (e.g., an image) on a display (not shown). Calibration memory unit 154 stores camera aberration-free images (or models) $174_1$, . . . , $174_N$. Hence, for each one of calibration images $172_1$, . . . , $172_N$ acquired at different viewpoints (i.e., having specific position) of calibration camera 156 in HMD reference frame 122, there is an associated and respective camera aberration-free image $174_1$, . . . , $174_N$ corresponding to that viewpoint (i.e., a pair-wise association denoted according to identical index value). Calibration processor 152 is configured to make this pair-wise association. Specifically, for calibration image $172_1$, acquired by calibration camera 156 at P(1), there exists a camera aberration-free image $174_1$. Likewise for calibration image $172_2$ acquired at P(2) there exists a camera aberration-free image (or model thereof) 1742, and so forth. More specifically, for each (i, j) pixel in each of calibration images $172_1$, $172_2$, . . . , $172_N$ there is associated with a corresponding (k, l) pixel in respective camera aberration-free images $174_1$, 1742, . . . , $174_N$. In general, the aberration-free images are not generated simply by shifting by an integer number of pixels, but rather involve interpolation of neighboring pixels. Without unnecessarily complicating the description of the disclosed technique, it is assumed that the images are two-dimensional (2-D). Hence, pixel (i, j) in calibration image $172_1$, denoted by $172_1^{(i,j)}$ is associated with pixel (k, l) in camera aberration-free image $174_1$, denoted by $174_1^{(k,j)}$, and so forth to N. The pair-wise association, as well as the (i, j)-to-(k, l) pixel association forms part of camera aberration correction data 176 (reference data).

Figure 5B:
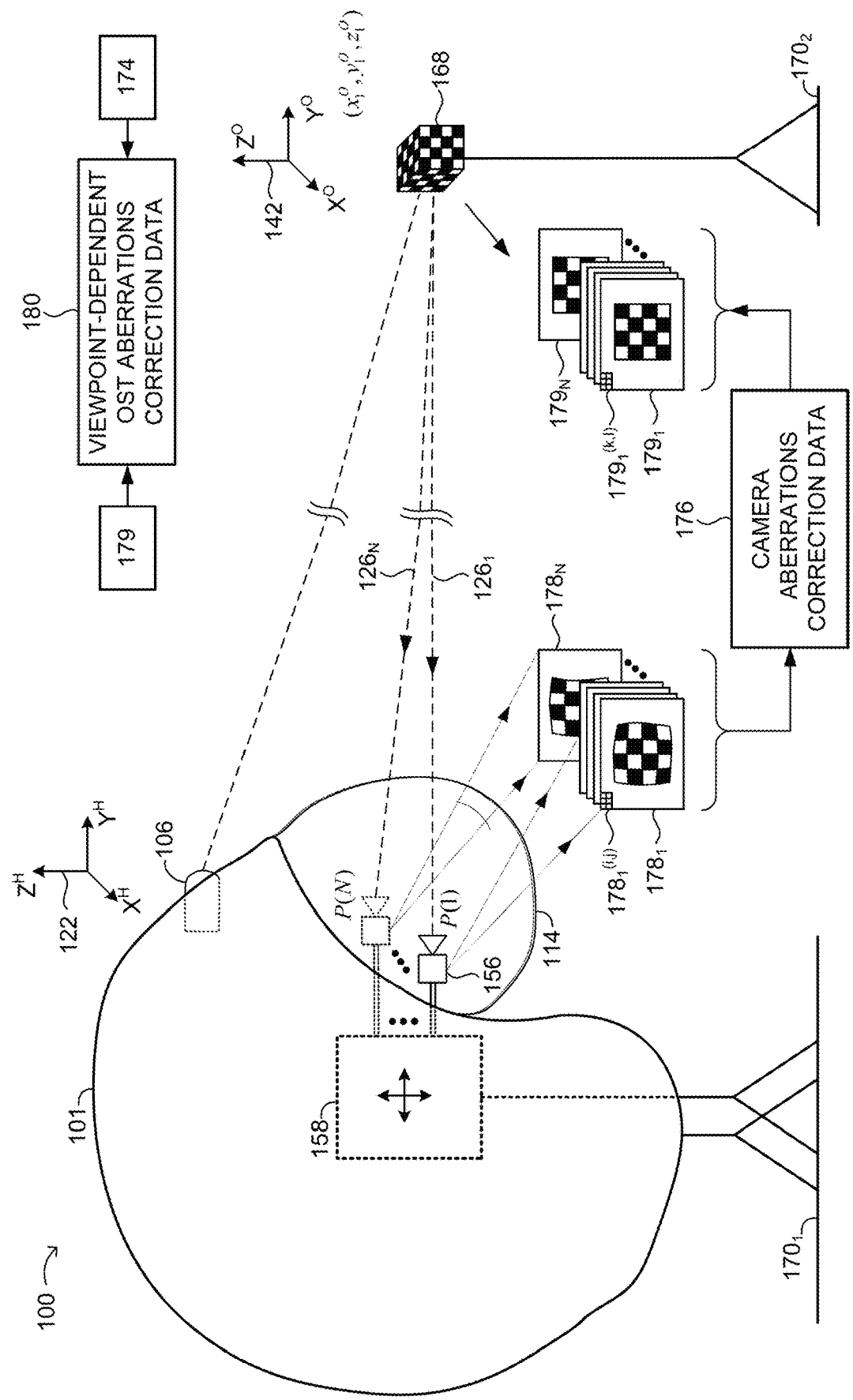
FIG. 5B is a schematic diagram showing a second phase in the calibration procedure of OST HMD system, constructed and operative in accordance with the embodiment of the disclosed technique.

Reference is now further made to FIG. 5B, which is a schematic diagram showing a second phase in the calibration procedure of OST HMD system, constructed and operative in accordance with the embodiment of the disclosed technique. The second phase in the initial calibration procedure determines a viewpoint-dependent optical see-through (OST) aberrations correction data 180. Hence, the second phase involves the determination of correction data for rectifying OST aberrations for different positions (viewpoints) of calibration camera 156. OST aberrations (including distortions) are mainly due to the interaction (e.g., refraction) between light from calibration object 168 (represented by chief rays $126_1$, . . . , $126_N$ for P(1) to P(N), respectively) and partially reflective partially transmissive optical element 114. These OST aberrations are essentially caused by optical aberrations of partially reflective partially transmissive optical element 114 (e.g., due to its spatial geometrical properties such as curvature (e.g., bringing about prismatic distortion effects), as well as optical characteristics such as refractive index, etc.).

Calibration camera 156 is configured and operative to capture a plurality of calibration images $178_1$, . . . , $178_N$ of calibration object 168, through partially reflective partially transmissive optical element 114. Calibration processor 152 and/or calibration memory unit 154 receive/s calibration images $178_1$, . . . , $178_N$ from calibration camera 156. For each calibration image $178_1$, . . . , $178_N$, calibration processor 152 is configured and operative to produce a respective camera aberration-free image (or model) $179_1$, . . . , $179_N$ associated therewith. Hence, for each calibration image $178_1$, . . . , $178_N$ there exists a respective (index-wise) camera aberration-free image $179_1$, . . . , $179_N$, for each of N positions and orientations of calibration camera 156.

As shown in FIG. 5B, calibration processor 152 (FIG. 4) receives calibration images $178_1$, . . . , $178_N$, and uses camera aberrations correction data 176 to produce OST distorted images $179_1$, . . . , $179_N$. Calibration processor 152 uses OST distorted images $179_1$, . . . , $179_N$, and camera aberration-free images $174_1$, . . . , $174_N$ and is configured and operative to produce (e.g., estimate, compute) viewpoint-dependent OST aberrations correction data 180 for each one of respective N positions of calibration camera 156 (as shown in the top-right block diagram of FIG. 5B). Calibration memory unit 154 is configured and operative to store viewpoint-dependent OST aberrations correction data 180 therein. The term "correction" and derivative words thereof, used herein in the context of OST aberration correction data, refer to a process or method of substantially negating, reversing, or compensating (for) the effects of optical aberrations of partially reflective partially transmissive optical element 114.

Various methods may be utilized to compute viewpoint-dependent OST aberrations correction data 180, for example, by using feature (e.g., pixel) mapping (transformation) techniques, by performing an image-to-image comparison (according to index) of image properties of calibration images $179_1$, . . . , $179_N$ with image respective image properties of OST aberration-free images $174_1$, . . . , $174_N$. Example properties used in the comparison may include spatial geometrical features, dimensions, relative orientation, and the like. Another example includes performing a point-by-point or pixel-wise comparison of an (i, j) pixel of calibration image $179_1$ with a corresponding (k, l) pixel of camera aberration-free image $174_1$, and respectively so forth for each associated image pair up to N.

Figure 5C:
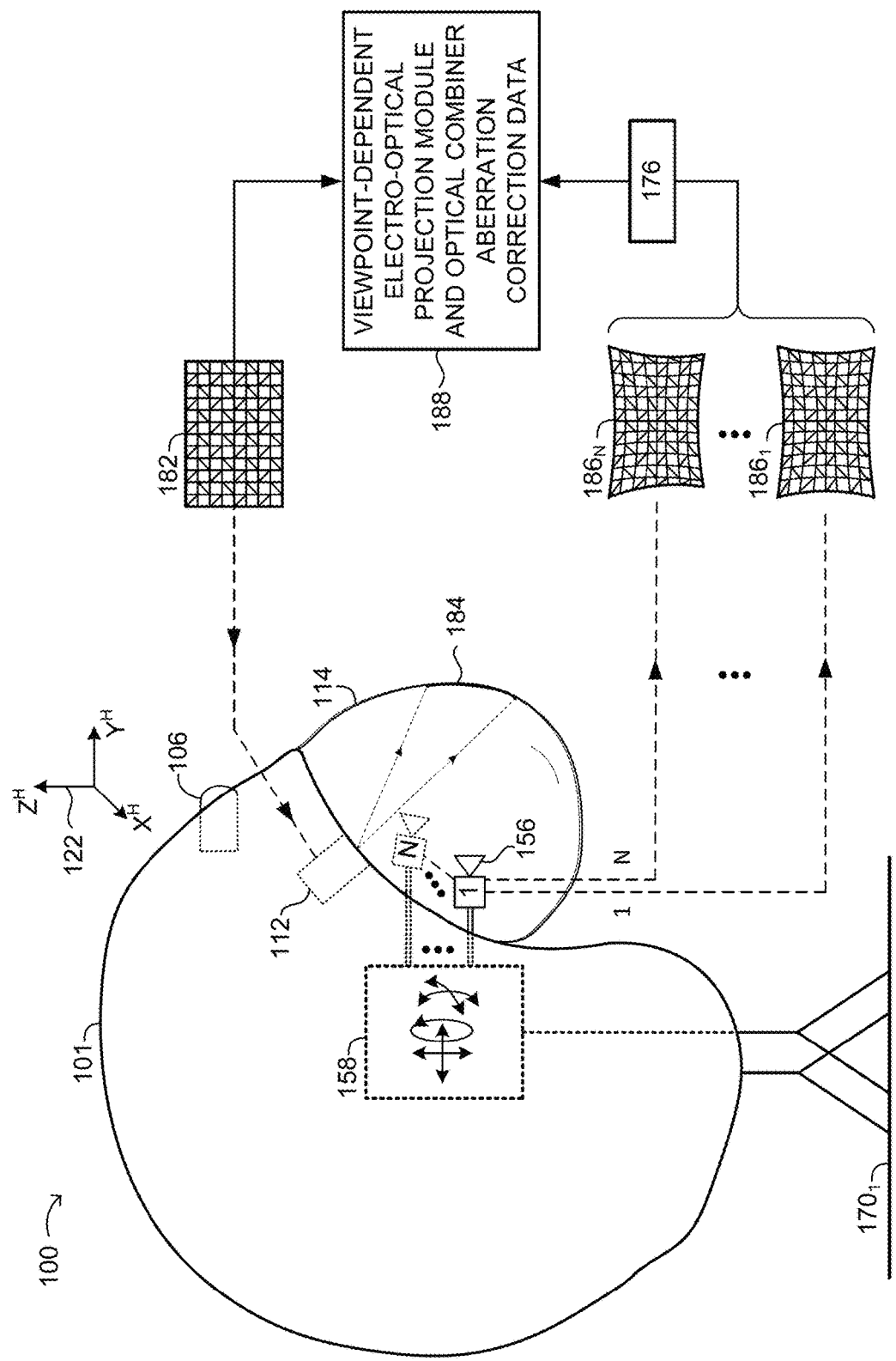
FIG. 5C is a schematic diagram showing a third phase in the calibration procedure of OST HMD system, constructed and operative in accordance with the embodiment of the disclosed technique.

Reference is now further made to FIG. 5C, which is a schematic diagram showing a third phase in the example calibration procedure of OST HMD system, constructed and operative in accordance with the embodiment of the disclosed technique. Without loss of generality, the third phase calibration procedure describes a particular example involving a curved (e.g., spherical) optical combiner 114, however, the principles of this calibration procedure apply to other display techniques such as waveguide projection techniques (not shown), and the like. The third phase in the calibration procedure involves determining viewpoint-dependent aberration correction data 188 of electro-optical projection module 112 and optical combiner 114, both corrected together (hereinafter interchangeably "viewpoint-dependent electro-optical projection module and optical combiner aberration correction data 188"). In particular, electro-optical projection module 112 irradiates and projects light encoded with information, such as in the form of an image 184, which in turn is partially reflected from partially reflective partially transmissive optical element 114 toward calibration camera

156. Image 184 (or a plurality of images for that matter) may exhibit aberrations that are intrinsic to electro-optical projection module 112, as well as aberrations that are extrinsic, arising for example, from an off-axis position of electro-optical projection module 112. In addition, the reflection of image 184 off a curved projection surface of partially reflective partially transmissive optical element 114 will also exhibit aberrations to its appearance when acquired by calibration camera 156.

In accordance with the third phase in the calibration procedure, the aforementioned effects are countered. In particular, calibration processor 152 transmits a calibration image 182 to electro-optical projection module 112, which in turn irradiates and projects it onto partially reflective partially transmissive optical element 114 as image 184. Calibration camera 156 is configured and operative to acquire images from a plurality of N camera viewpoints (i.e., P(1), . . . , P(N)), and to respectively output reflected calibration image 1861 (captured from P(1)), reflected calibration image 1862 (captured from P(2)—not shown), and so forth up to reflected calibration image 186N (captured from P(N)). Calibration processor 152 receives reflected calibration images 1861, . . . , 186N from calibration camera 156 and/or via calibration memory unit 154. Calibration processor 152 is configured and operative to produce viewpoint-dependent electro-optical projection module aberration correction data 188, given calibration image 182, and reflected calibration images 1861, . . . , 186N, and camera aberrations correction data 176, by employing various techniques. Example techniques include methods of image transformation on a feature or pixel-wise basis (image warping) for spatial (geometric) aberration compensation (correction). According to one image transformation method, calibration processor 152 determines N different transformations for N respective viewpoints of calibration camera 156. Each transformation defines how pixels or groups of pixels in a reflected calibration image are mapped to respective location-similar pixels or groups of pixels of calibration image 182, taking into account camera aberration correction data 176 (FIGS. 5A and 5B) of calibration camera 156. Hence, viewpoint-dependent electro-optical projection module aberration correction data 188 enables the transformation of reflected calibration images 1861, . . . , 186N acquired from N viewpoints to be corrected before they are projected so as to take into account aberrations of electro-optical projection module 112 to yield electro-optical projection module aberration-free images when viewed from various eye positions.

As will be hereinafter described in greater detail, replacing calibration camera 156 with eye 14 of user 10 wearing helmet 101 (post-calibration), and subsequently determining eye 14 position via eye position determination module 108 (FIG. 2) enables to associate eye 14 position with one of P(1), . . . , P(N). Processor 102 (FIG. 2) receives eyeball feature position data generated from eye position determination module 108 and associates viewpoint-dependent electro-optical projection module aberration correction data 188 corresponding to one of the viewpoints P(1), . . . . P(N). Generally, (and in case) a determined eye position does not precisely correspond with one of positions P(1), . . . , P(N), processor 102 is configured and operative to derive appropriate correction data corresponding to that eye position by interpolating from correction data associated with at least one closest matching position (i.e., one of P(1), . . . , P(N)). Processor 102 is configured to derive from the correction data, closest-matching correction data that is associated with at least one closest matching position. The eyeball feature position data may have a higher resolution than the resolution of the predetermined information (e.g., calibration data) (e.g., millimeter resolution versus sub-millimeter resolution). Alternatively, the eyeball feature position data is truncated (i.e., approximated, rounded) by eye position determination module 108. For example, when a determined eye position falls exactly in between two positions P(i) and P(j), processor 102 may generate the correction data by averaging the correction data associated with P(i) and P(j). Thereafter, processor 102 directs electro-optical projection module 112 to irradiate and project image 184 that is pre-distorted or compensated according to one of the corresponding viewpoints, such that when it is reflected off partially reflective partially transmissive optical element 114 it appears or perceived to be substantially aberration-free (i.e., although the projected image is itself distorted as well as the real-world view as seen through partially reflective partially transmissive optical element 114).

The fourth phase in the calibration procedure involves the construction of unified correction data as a function of N different positions of calibration camera, according to the preceding phases (i.e., first, second and third) of the calibration procedure. Reference is now further made to FIGS. 6A, 6B, 6C, 6D, and 6E, which demonstrate how data attained from preceding calibration steps are compounded to arrive at unified correction data that may be represented in the form of a lookup table. FIGS. 6A-6E show the fourth phase in the calibration procedure.

Figure 6E:
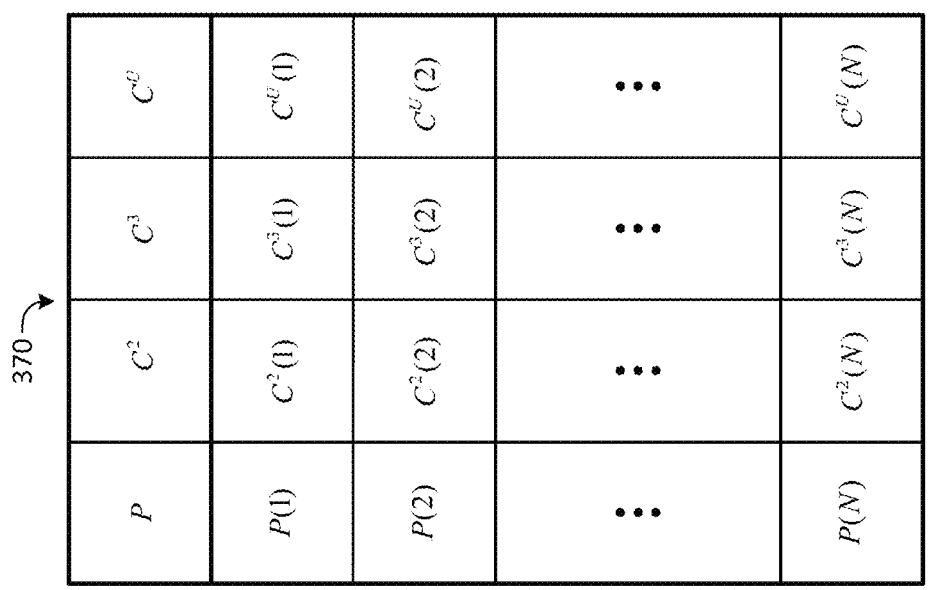

Specifically, FIG. 6A is a schematic illustration showing the effect of not correcting the eye position of a user, and OST aberrations, and electro-optical projection module and optical combiner aberrations. FIG. 6B is a schematic illustration showing the effect of correcting the eye position of a user, but not correcting for OST aberrations, and electro-optical projection module and optical combiner aberrations. FIG. 6C is a schematic illustration showing the effect of correcting for eye position of a user, and OST aberration correction, but not of correcting for electro-optical projection module and optical combiner aberrations. FIG. 6D is a schematic illustration showing the effect of correcting for the eye position of a user, OST aberration correction, and electro-optical projection module and optical combiner aberrations. FIG. 6E is a schematic block diagram illustrating a representation of the unified correction data in the form of a lookup table.

FIG. 6A shows electro-optical projection module 112 and optical combiner 114, an (externally viewed) object 192, two rays 194 and 196, and two positions: P (i.e., the actual position of the user's eye), and DEP (design eye position) (i.e., a default assumed eye position in an HMD without an eye position determination capability). Electro-optical projection module 112 projects image 184 onto optical combiner 114 that includes a single object, namely, a rectangle supposed being in alignment with object 192 as seen through the HMD (i.e., the aim is for a rectangle 200 to appear to the user symmetrically enclosing object 192 (i.e., object 192 is at the center of rectangle 200). For example, in pilot applications, such alignment may be used to emphasize a target for a pilot). Rectangle 200 is a simplified representation of what the user may see when looking through optical combiner 114. Rectangle 200 includes an object denoted by dot 204 and a virtual rectangle denoted by 202. In a situation where the actual position P of the eye is unknown, and without viewpoint dependent OST aberrations correction and electro-optical projection module and optical combiner aberrations correction, virtual rectangle 202 appears to the user above a perceived position 198 of object 192 as seen through optical combiner 114 (represented by dot 204). Specifically, light ray 194 represents an exemplary light path from the DEP to object 192, and light ray 196 represents an exemplary light path from a position P passing through optical combiner 114 that is astray. For the sake of simplicity of explaining the disclosed technique, the intersection of light rays 194 and 196 denoted by 190 is at optical combiner 114 and it is where image 200 of virtual rectangle 202 appears to user. Note that operationally image 200 is not focused at optical combiner 114 but further away, although the principles of the disclosed technique apply likewise for different focus distances. Dot 204 represents perceived position 198 of object 192 to the user looking through optical combiner 114 due to see-through distortions, although the real position of object 192 is displaced from perceived position 198.

Reference is now made to FIG. 6B, which shows the same hardware features as in FIG. 6A apart from the inclusion of eye position determination module 108. FIG. 6B is a schematic illustration showing the effect of correcting the eye position of a user, but not correction for OST aberrations, and electro-optical projection module and optical combiner aberrations. Electro-optical projection module 112 projects image 205 onto optical combiner 114. Eye position determination module 108 determines an eye position at point P. A light ray 210 represents an exemplary light path from determined user eye position P through optical combiner 114 to object 192. The user, however, perceives the position of object 192 at a position denoted by dot 198. FIG. 6B shows the effect of correcting the eye position of the user, but not the correction of OST aberrations, and electro-optical projection module and optical combiner aberrations. With only corrections to the eye position of the user, virtual rectangle 216 in the FOV 200 seen by the user below a perceived position 198 of object 192 (as denoted by dot 204).

Reference is now made to FIG. 6C, which shows the same hardware features as in FIG. 6B. FIG. 6C is a schematic illustration showing the effect of correcting the eye position of a user and correcting for OST aberrations (see-through distortions), but not correcting for electro-optical projection module and optical combiner aberrations (display distortions). Electro-optical projection module 112 projects image 206 onto optical combiner 114.

Eye position determination module 108 determines an eye position at point P. A light ray 230 represents an exemplary light path from determined user eye position P through optical combiner 114 to a perceived position 198 of object 192, as it appears to a user 15 through optical combiner 114.

With corrections to the eye position and corrections of OST aberrations, but without the display correction, a virtual rectangle 238 in FOV 200 as seen by the user appears slightly below its desired position around the perceived position 198 of object 192 (as denoted by dot 204).

Reference is now to FIG. 6D, which shows the same hardware features as in FIG. 6C. FIG. 6D is a schematic illustration showing the effect of correcting for the eye position of a user, OST aberration correction (see-through corrections), and electro-optical projection module and optical combiner aberrations (display corrections). Electro-optical projection module 112 projects image 207 onto optical combiner 114. Eye position determination module 108 determines an eye position at point P. A light ray 242 represents an exemplary light path from determined user eye position P through optical combiner 114 to a perceived position 198 of object 192, as it appears to a user through optical combiner 114. With the combined corrections to the position of the eye of the user, see-through corrections of optical combiner 114, as well as display corrections, a virtual rectangle 250 is properly superimposed with a perceived position 198 of object 192 (as denoted by dot 204 located centrally with respect to virtual rectangle 250). As indicated above, with regard to the basic configuration, eye position determination module 108 is not part of OST HMD system and the corresponding calibration phase shown in FIGS. 6A-6D may be implemented by receiving eyeball feature position data generated by any of the methods detailed in the basic configuration.

FIG. 6E illustrates an example representation of a unified correction data (database) having the form of a lookup table 370. Lookup table 370 tabulates the position-dependent corrections $C^2$, $C^3$, $C^U$ for each one of N positions $P(1), \ldots, P(N)$. Correction $C^2$ in the calibration procedure represents the second phase correction, i.e., viewpoint-dependent OST aberrations correction data 180 (FIG. 5B). Correction $C^3$ in the calibration procedure represents the third phase, i.e., viewpoint-dependent electro-optical projection module and optical combiner aberration correction data 188 (FIG. 5C). Ultimately, the respective corrections $C^2$, and $C^3$ in the calibration procedure in lead to unified correction data $C^U$. In general, the disclosed technique is compatible with various types of calibration procedures so long that the end result is unified correction data $C^U(N)$ for each of N positions, as may be represented by look-up table 370.

Generally, for each one of positions $P(1), \ldots, P(N)$ there corresponds respective (index-wise) position-dependent unified correction data $C^U(1), \ldots, C^U(N)$. Specifically, for position P(1) there corresponds a position-dependent unified correction data $C^U(1)$, as well as corrections $C^2(1)$, $C^3(1)$; for position P(2) there corresponding a position-dependent unified correction data $C^U(2)$, as well as corrections $C^2(2)$, $C^3(2)$, and so forth to N. The unified corrections (denoted by the "U" superscript) represent compounded corrections taken into account at each individual step, for each N different eye positions. Specifically, C (1) represents the unified correction corresponding to eye position 1, C (2) represents the unified correction corresponding to eye position 2, and so forth to $C^U(N)$ for eye position N. The unified corrections may depend on the parameterization used. In effect, and for example, without any correction an image of a symbol is intended for being displayed at a symbol location (x, y), but instead, a first correction corrects the intended symbol location to $(x_1, y_1)$, the second correction further corrects the symbol location to $(x_2, x_2)$, such that the corrections are compounded to attain the unified correction for a symbol location $(x_u, y_u)$, so that the image of the symbol appears to the user superimposed in an aligned manner with respect to an outwardly viewed object (e.g., a real object, a virtual object (image), a completely hidden object, a partially hidden object).

Figure 7:
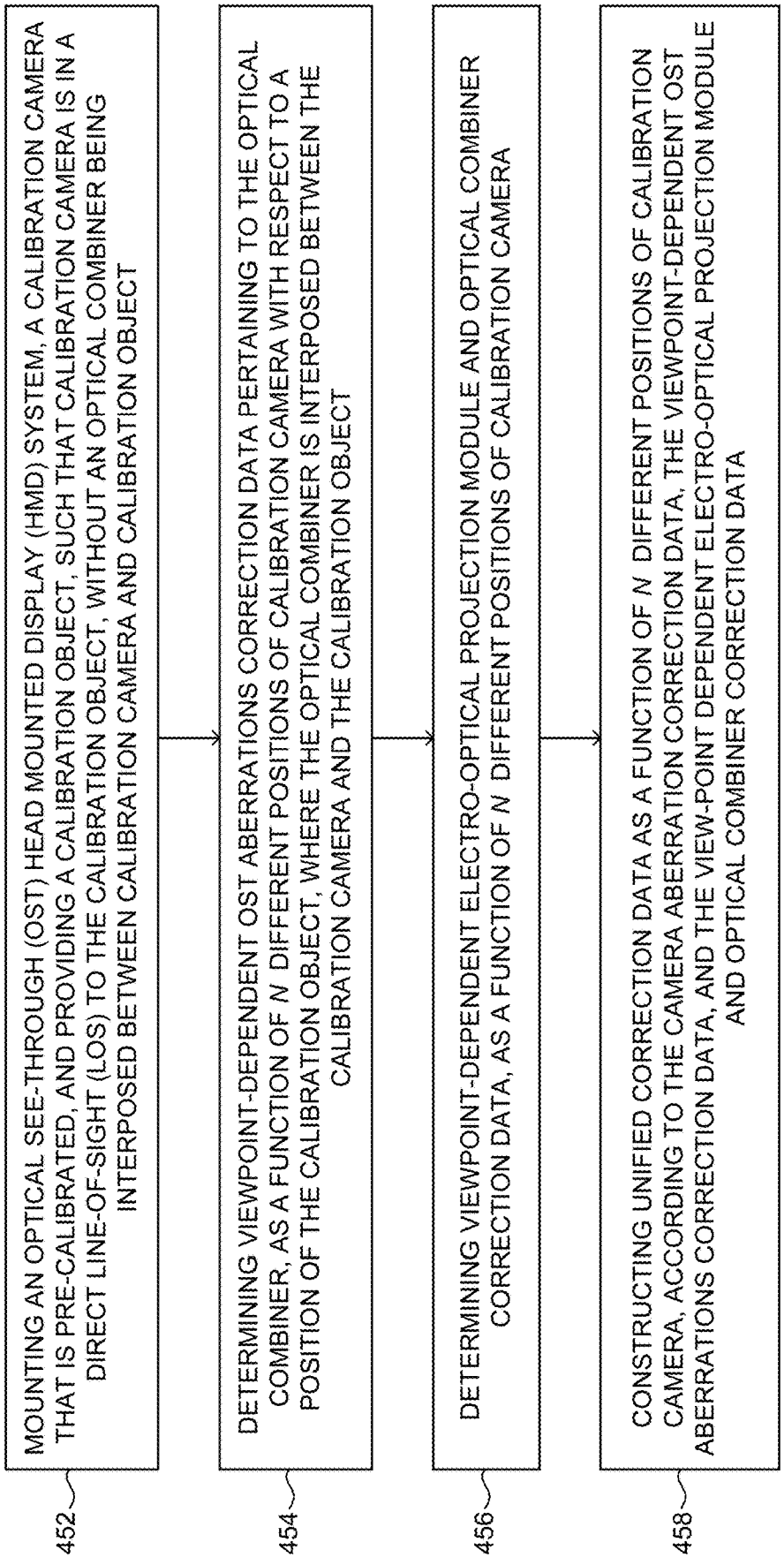
FIG. 7 is a schematic block diagram of a method, illustrating steps in the initial calibration procedure, constructed and operative in accordance with the embodiment of the disclosed technique.

Reference is now made to FIG. 7, which is a schematic block diagram of a method, generally referenced 450, illustrating steps in the initial calibration procedure, constructed and operative in accordance with the embodiment of the disclosed technique. Method 450 initiates with procedure 452. In procedure 452, a calibration object is provided, and an optical see-through (OST) head mounted display (HMD) system and a calibration camera that is pre-calibrated, are mounted on at least one platform, such that the calibration camera is in a direct line-of-sight (LOS) to calibration object, without an optical combiner being interposed between calibration camera and calibration object. With reference to FIGS. 2, 3, 4, 5A, and 7, OST HMD system 100 (FIG. 5A), calibration camera 156 (FIGS. 4 and 5A), and calibration object 168 (FIGS. 4 and 5A) are mounted on platforms 1701 (OST HMD system 100 and calibration camera 156) and 1702 (calibration object 168), such that calibration camera 156 is in a direct LOS to calibration object 168, without optical combiner (FIGS. 2 and 3) being interposed between calibration camera 156 and calibration object 168.

In procedure 454, viewpoint-dependent OST aberrations correction data pertaining to the optical combiner, as a function of N different positions of calibration camera with respect to a position and orientation of calibration object is determined. The optical combiner is interposed between the calibration camera and the calibration object. With reference to FIGS. 4, 5A and 5B, calibration processor 152 (FIG. 4) determines viewpoint-dependent OST aberrations correction data 180 (FIG. 5B) taking into account camera aberration correction data 176 (FIG. 5A), for N different positions, P(1), . . . , P(N), of calibration camera 156 (FIGS. 4 and 5B) with respect to a position and orientation of calibration object 168 (FIGS. 4 and 5B). Optical combiner 114 is interposed between (FIG. 5B) calibration camera 156 and calibration object 168.

In procedure 456, viewpoint-dependent electro-optical projection module and optical combiner correction data is determined, as a function of N different positions of the calibration camera is determined. With reference to FIGS. 4 and 5C, calibration processor 152 (FIG. 4) determines viewpoint-dependent electro-optical projection module and optical combiner aberration correction data 188 (FIG. 5C) pertaining to electro-optical projection module 112 (FIG. 5C). Electro-optical projection module 112 projects calibration image 182 (FIG. 5C) toward optical combiner 114 (FIG. 5C), which in turn, reflects reflected calibration image 184 (FIG. 5C) toward calibration camera 156. Calibration camera 156 captures a plurality of N calibration images 1861, . . . , 186N (FIG. 5C) of reflected calibration image 184, from N respective positions P(1), . . . , P(N).

In procedure 458, unified correction data as a function of N different positions of calibration camera is constructed, according to the camera aberration correction data, the viewpoint-dependent OST aberrations correction data, and the viewpoint-dependent electro-optical projection module and optical combiner correction data. With reference to FIGS. 4, 5A, 5B, 5C, and 6A-6E, calibration processor 152 (FIG. 4) constructs unified correction data 370 (FIG. 6E) as a function of N different positions P(1), . . . , P(N) (FIGS. 5A-5C, 6A-6E) of calibration camera 156, according to viewpoint-dependent OST aberrations correction data 180 (FIG. 5B), and viewpoint-dependent electro-optical projection model aberration and optical combiner correction data 188 (FIGS. 5C, 6C). Unified correction data 370 (FIG. 6E) may be represented as a lookup table. Lookup table 370 represents a database of correction information that associates N correction data (or models) for each position P(1), . . . , P(N) in HMD reference frame 122.

Following the initial calibration procedure, OST HMD system 100 is ready for mounting onto head 12 of user 10 as shown in FIG. 3. The calibration data produced in the initial calibration procedure or at least a derivative thereof, including lookup table 370 is transferred to memory device 104 of OST HMD system 100 for retrieval. Once user 10 mounts OST HMD system 100 via HMD-to-head coupler 101 (e.g., in the form of helmet), calibration camera 152 is effectively replaced with eye 14 (FIG. 3) of user 10. Eye 14 of different users may assume a plurality of different eye positions (i.e., given different users having different relative eye-to-head positions, as well as different relative HMD-to-head positions). Eye position determination module 108 (FIGS. 2 and 3) is configured and operative to determine position data associated with a position of eye 14 with respect to OST HMD system reference frame 122. This position data may be partial (i.e., including only part of the position coordinates (e.g., x and y coordinate values, but not the z coordinate value in a Cartesian coordinate system)).

Figure 8B:
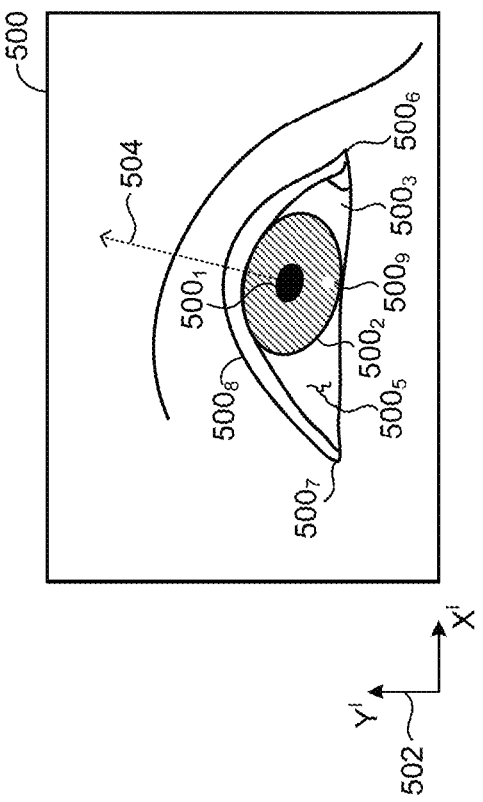
FIG. 8B is a schematic diagram showing an acquired image of the eye shown in FIG. 8A, constructed and operative in accordance with the embodiment of the disclosed technique.
Figure 8D:
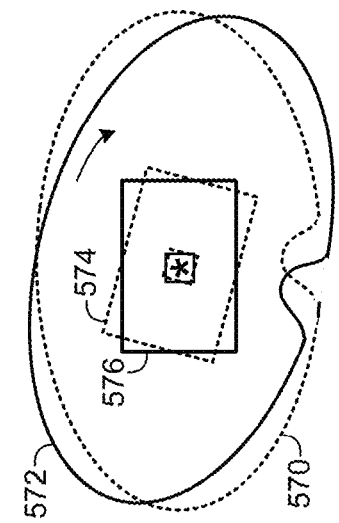
FIG. 8D is a schematic illustration showing orientation correction of a projected image with respect to a rotated orientation of OST HMD.
Figure 8A:
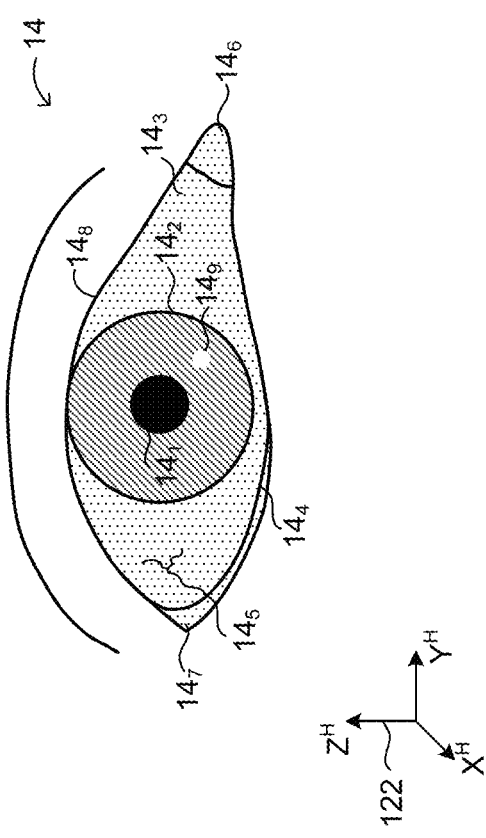
FIG. 8A is a schematic diagram showing various parts of an eye of a user, referred in the context of the disclosed technique.
Figure 8C:
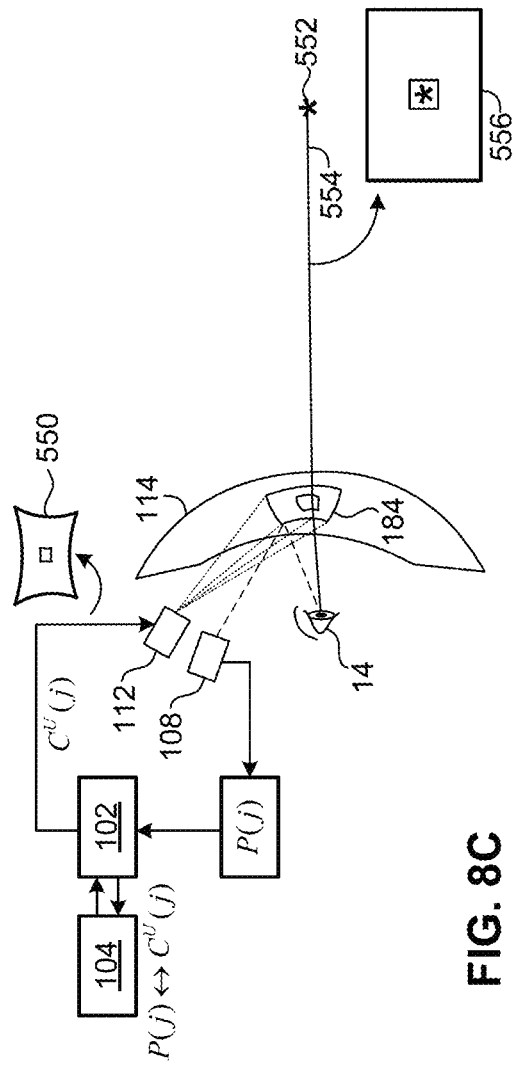
FIG. 8C is a schematic illustration showing use of unified correction data for providing real-time alignment between a projected virtual object on optical combiner and a real-world object as viewed by an eye of a user, constructed and operative in accordance with the embodiment of the disclosed technique.

To further elucidate the configuration, operation, and implementation OST HMD system 100, reference is now further made to FIGS. 8A, 8B, 8C, and 8D. FIG. 8A is a schematic diagram showing various parts of an eye of a user, referred in the context of the disclosed technique. FIG. 8B is a schematic diagram showing an acquired image of the eye shown in FIG. 8A, constructed and operative in accordance with the embodiment of the disclosed technique. FIG. 8C is a schematic illustration showing the use of unified correction data for providing real-time alignment between a projected virtual object on optical combiner and a real-world object as viewed by an eye of a user, constructed and operative in accordance with the embodiment of the disclosed technique. FIG. 8D is a schematic illustration showing orientation correction of a projected image with respect to a rotated orientation of OST HMD. FIG. 8A illustrates various typical examples of eyeball features of eye 14 of user 10 (FIG. 3), including for example, pupil 141, iris 142, sclera 143, conjunctiva 144, blood vessel 145, inside corner 146, outside corner 147, eye opening boundary 148, and the like. Eye position determination module 108 (FIG. 3) determines position data associated with at least one position of at least one eyeball feature (e.g., 141, 142, 143, 144, 145, 146, 147, etc.) of eye 14 of user 10 with respect to HMD reference frame 122, by various techniques. Eyeball feature detection techniques (i.e., used for determining eye position) are employed by the disclosed technique (e.g., video or still image oculography), typically involve capturing at least one image 500 (FIG. 8B) of eye 14 (i.e., or at least part thereof) via an image capture device (e.g., a camera) and deriving from the captured image eyeball feature positions that are correlated with HMD reference frame 122. An infrared (IR) light emitting diode (LED) may be used to illuminate eye 14. Eye position determination module 108 determines the position data associated with the position of eye 14 in HMD reference frame 122 according to the following steps. Eye position determination module 108 acquires (i.e., via a camera—not shown) an image 500 (FIG. 8B) of eye 14 (FIG. 8A), such that image 500 includes at least one (typically a plurality of) imaged eyeball feature(s), such as an image of pupil 5001, and image of iris 5002, image of sclera 5003, image of blood vessel 5005, image of inside corner 5006, image of outside corner 5007, image of eye opening boundary 5008, and the like.

Eye position determination module 108 defines a transformation (i.e., a mapping) between an image coordinate system 502 (FIG. 8B) and HMD reference frame 122 (coordinate system) so to construct a transformation (i.e., with respect to position) between eyeball features in HMD reference frame 122 and corresponding imaged eyeball features present in image 500. At least one imaged eyeball feature present in image 500 within image coordinate system 502 is associated with a respective real eyeball feature in HMD reference frame 122. It is noted that eye position determination module 108 may include more than one camera (not shown) for determining the eye position, so as to obtain an accurate 3-D eye position data (including depth). Alternatively, eye position determination module 108 employs other techniques, for example light beam (e.g., laser) scanning and sensing methods (not shown) to determine the eye position. When using a single camera, 2-D eye position is straightforwardly acquired from image 500, while a third dimension (i.e., depth in 3-D eye position data) may be also determined by various techniques, such as by knowing the size of eye 14, or eye ball features (e.g., pupil 141) based on known user-specific sizes. Alternatively or in addition, 3-D eye position data is determined via IR oculography as mentioned hereinabove. Particularly in this method (also denoted as the corneal specular reflection approach), at least one infrared (IR) light emitting diode (LED) (not shown) emits IR light that at least partially illuminates eye 14, an IR light sensor (not shown) detects the reflection or glint 149 (FIG. 8A), and processor 102 (FIG. 2) determines the glint size so as to assess 3-D eye position. Alternatively, in special cases the need to determine the exact eye position is skipped, and instead processor 102 guesses an eye position and relates the guessed eye position (or a guestimate position) with corresponding correction data. Further alternatively, instead of determining 3-D eye position, only 2-D eye position data is determined without greatly degrading accuracy.

With reference to FIG. 8C, eye position determination module 108 is configured and operative to determine the position of eye 14 with respect to OST HMD system reference frame 122. Processor 102 may facilitate in the eye position determination. Preferably, the determined position of eye 14 may correspond with one of positions P(1) . . . , P(N). The value of N as well as the density of positions within a given volume in space of HMD system reference frame 122 is related to the accuracy or resolution that is required. Generally, the greater the value of N and the greater the density of points or positions P(1), . . . P(N), the greater the chance of an arbitrary user's eye position to match one of P(1), . . . , P(N). Eye position determination module 108 is configured and operative to first determine position of eye 14 with respect to OST HMD system reference frame 122, and second to associate the determined position with one of positions P(1), . . . , P(N). In case the eye position data associated with the eye position does not precisely match (i.e., within predetermined tolerances) one of positions P(1) . . . . , P(N), eye position determination module 108 is configured to associate the determined eye position with the closest match (i.e., one of positions P(1), . . . , P(N)). Either one of processor 102 and eye position determination module 108 is configured to select one of positions P(1), . . . , P(N) in a situation where there is more than one closest matching position (e.g., two closest matching position values). Alternatively, as aforementioned, in case a determined eye position does not precisely correspond with one of positions P(1), . . . , P(N), processor 102 is configured and operative to derive appropriate correction data corresponding to that eye position by use of interpolation.

Once eye position determination module 108 determines eye 14 position, e.g., P(j), it provides (e.g., transmits) the result to processor 102, which in turn retrieves from memory device 104 (i.e., lookup table 370 stored therein, FIG. 6E) unified correction data, $C^U(n)$ associated with the n-th determined position P(n), where n is an integer: $0 < n \le N$. Based on the unified correction data, processor 102 is configured to generate an image 550 (i.e., in the form of data ("image data"), this image is pre-distorted) and to provide this image to electro-optical display module 112, which in turn is configured and operative to irradiate and project the image onto optical combiner 114 (represented as partially reflected image 184 in FIG. 8C). Projected and partially reflected image 184 appears to eye 14 of user 10 to be superimposed in an aligned manner with respect to object 552 (similar to object 168 (FIG. 3), located externally to OST HMD and appearing in the LOS 554 of user), as exemplified by (perceived) image 556. Hence, in real-time, processor 102 uses the position of eye 14 in the HMD reference frame 122 (i.e., helmet coordinate system), and the exact position and orientation (P&O) of the OST HMD or helmet relative to object 552, to determine (via eye position determination module 108) the position of user's eye 14 relative to object 552. Processor 102 takes this P&O into consideration for generating image 550 such that virtual object(s) in image 550 appear(s) overlaid in an aligned manner with respect to (real) object 552 when viewed from the currently determined eye position.

Processor 102 is configured and operative to associate and register a current determined eye position outputted by eye position determination module 108 with a one of the N different positions P(1), . . . . P(N) that were registered by calibration camera 152. For example, this association and registration may be performed in accordance with the closest match (e.g., via error minimization techniques). Processor 102 applies the appropriate correction model to image 146 (FIG. 3) or image 550 (FIG. 8C) according to the current detected position of eye 14, such that reflected image 144 (FIG. 3) or image 184 (FIG. 8C) appears in an aligned position and orientation with respect to external object 140 located outwardly to the user through optical combiner 114, as representatively illustrated in FIG. 3 by a superimposed image 148 and in FIG. 8C by superimposed (perceived) image 556.

With reference to FIG. 8D, tracking system 106 (FIG. 2), processor 102, and electro-optical projection module 112 are further configured and operative to correct the orientation of a projected image when head 12 of user and thereby OST HMD system 100 (and/or helmet 101) rotates with respect to an orientation of an externally viewed object. FIG. 8D shows a particular example of a typical field-of-view (FOV) of OST HMD 100 being at a reference orientation, denoted by 570 (dotted line). The example shown in FIG. 8D is representative of a limited case having one degree-of-freedom (DOF) in which the user's head 12 rotates about a center axis, and the object visualized is positioned exactly at this center axis. When user's head 12 rotates (i.e., rolls around the center axis), the current OST HMD FOV 572 rotates correspondingly (arrow) with respect to the reference (noncurrent) OST HMD FOV 570. Tracking system 106 is configured to detect changes in the orientation of OST HMD 100 (or head 12) with respect to previous orientations, and also with respect to external (real or virtual) object (e.g., horizon). Tracking system 106 outputs data indicative of these changes and provides this data to processor 102, which in turn is configured to direct electro-optical projection module 112 to project an orientation-corrected image 576 onto optical combiner 114, such that orientation of orientation-corrected image 576 matches the reference orientation (i.e., reference OST HMD FOV 570). Without correction, the projected image would be rotated along with the rotation of OST HMD FOV 572, as shown by orientation-uncorrected image 574 (dotted line). For the sake of simplicity, the example shown in FIG. 8D only shows a particular 1-DOF case, as for a more general 6-DOF case, HMD azimuth, elevation, and position are also taken into consideration.

Figure 9:
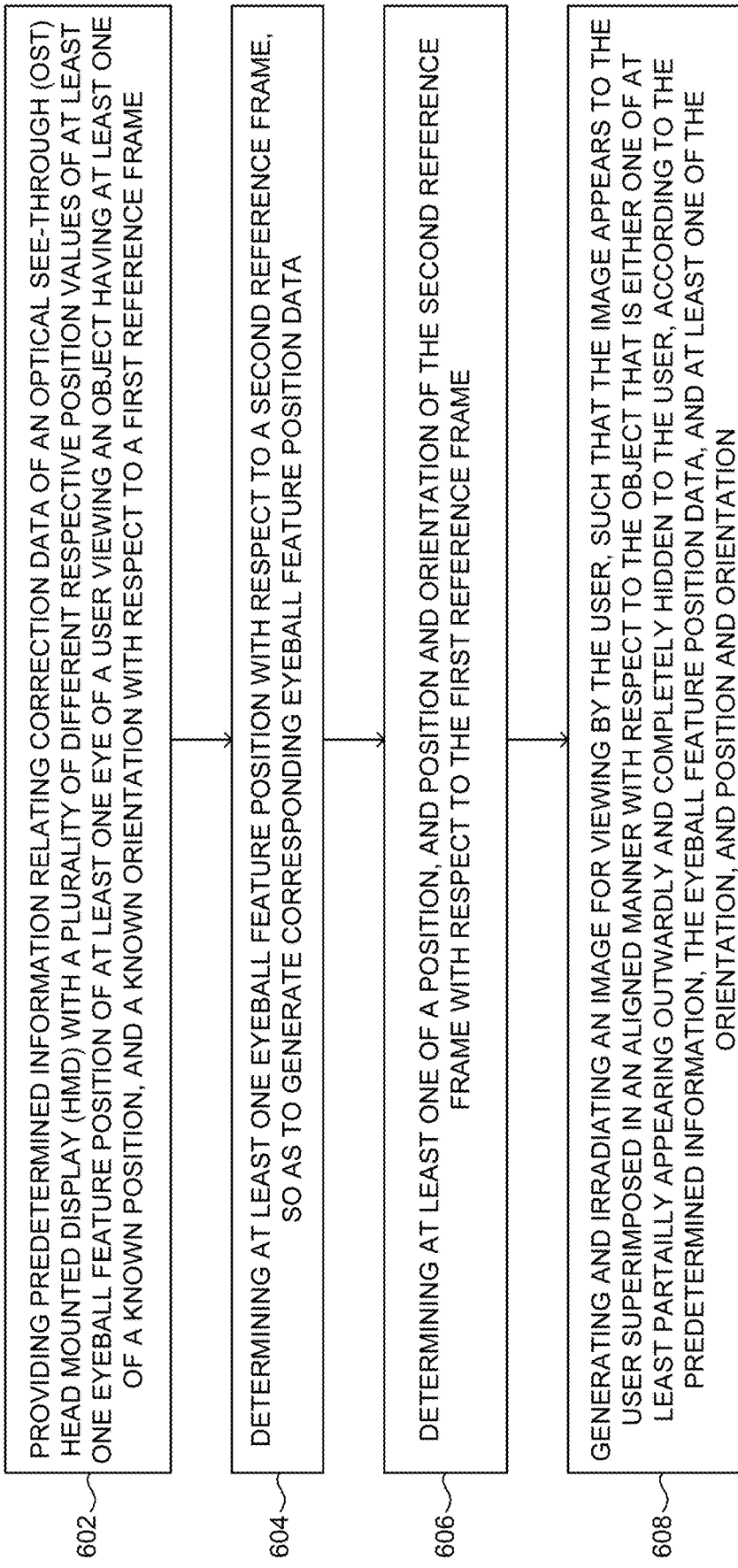
FIG. 9 is a schematic block diagram illustrating the steps of a method, constructed and operative in accordance with the disclosed technique.

Eye position determination module 108 may optionally be further configured and operative to estimate a gaze vector 504 (FIG. 8B) of eye 14 that defines an estimated looking direction or orientation of eye 14 by image processing methods and algorithms, such as those employing contour detection (e.g., of pupil 141 relative to iris 142 and relative to eye opening boundary $14_8$, or between other eye feature combinations), via the pupil-center-corneal reflection (PCCR) method, and the like. For a precise estimate of gaze vector 504 a calibration procedure may be typically required. The disclosed technique does not necessitate determination of gaze vector 504, as typically, an average position of eye may be sufficient. A typical example situation where only the average eye position is sufficient may be when head 12 of user 10 turns so that the target (e.g., object 140) is seen more or less along a center axis of the optical combiner 114 that is illuminated with a displayed image. Reference is now made to FIG. 9, which is a schematic block diagram illustrating the steps of a method, generally referenced 600, constructed and operative in accordance with the disclosed technique. Method 600 initiates with procedure 602. In procedure 602, predetermined information is provided that relates correction data of an OST HMD with a plurality of different respective position data values of at least one eyeball feature position of at least one eye of a user viewing an object having at least one of a known position, and a known orientation with respect to a first reference frame. With reference to FIGS. 3, 4, 5A-5C, and 6A-6E which relate to a calibration method that includes four phases implemented by an OST HMD calibration system 150 (FIG. 4), for generating unified correction data 370 (FIG. 6E) in the form of lookup table. Unified correction data 370 includes different respective position data values $P(1), \ldots, P(N)$ of at least one eyeball feature (FIG. 8A) position of at least one eye 14 (FIG. 3) of user 10 viewing at least one object 140 (FIG. 3) or object 191 (FIG. 6C) having at least one of a known position $(x_1°, y_1°, Z_1°)$ and a known orientation $(\beta\alpha_1°, \beta_1°, \gamma°)$ with respect to a first reference frame 142.

In procedure 604, at least one eyeball feature position with respect to a second reference frame is determined, so as to generate corresponding eyeball feature position data. With reference to FIGS. 2, 3, 8A, 8B, eye position determination module 108 (FIGS. 2 and 3) determines at least one eyeball feature (FIG. 8A) position (FIG. 8B), so as to generate corresponding eyeball feature position data $P(1), \ldots, P(N)$.

In procedure 606, at least one of a position, and position and orientation of the second reference frame is determined with respect to the first reference frame. With reference to FIGS. 2 and 3, tracking system 106 (FIG. 2) and processor 102 determine at least one of a position, and position and orientation of the second reference frame 140 (FIG. 3) with respect to the first reference frame 122 (FIG. 3). In procedure 608, an image for viewing by the user is generated and irradiated, such that the image appears to the user superimposed in an aligned manner with respect to the object that is either one of at least partially appearing outwardly and completely hidden to the user, according to the predetermined information, the eyeball feature position data, and the at least one of the orientation, and position and orientation. With reference to FIGS. 2, 3, 6D, 6E, and 8C, processor 102 (FIG. 2) generates image 146 (FIG. 3) or image 550 (FIG. 8C) that electro-optical projection module 112 (FIG. 3) irradiates and projects onto optical combiner 114 (FIGS. 3, 8C), such that the projected image appears to eye 14 (FIGS. 3, 8C) of user 10 superimposed in an aligned manner with respect to object 140 (FIG. 3) or object 552 (FIG. 8C) appearing outwardly to the user, according to the predetermined information (unified correction data (lookup table 370, FIG. 6E), eyeball feature position data $P(1), \ldots, P(N)$, as well as according to the relative P&O between the HMD and the object).

Figure 10C:
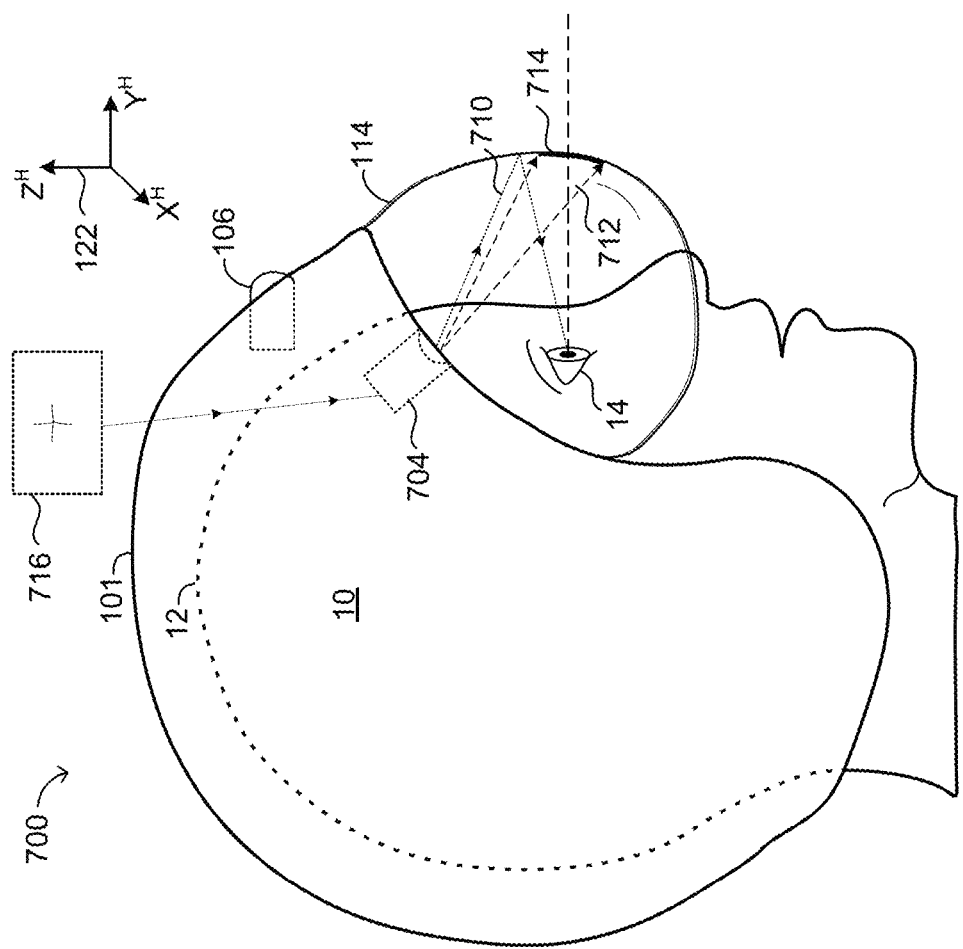
FIG. 10C is a schematic illustration showing a high-level configuration and operation aspects of the OST HMD system of FIG. 10A.
Figure 10A:
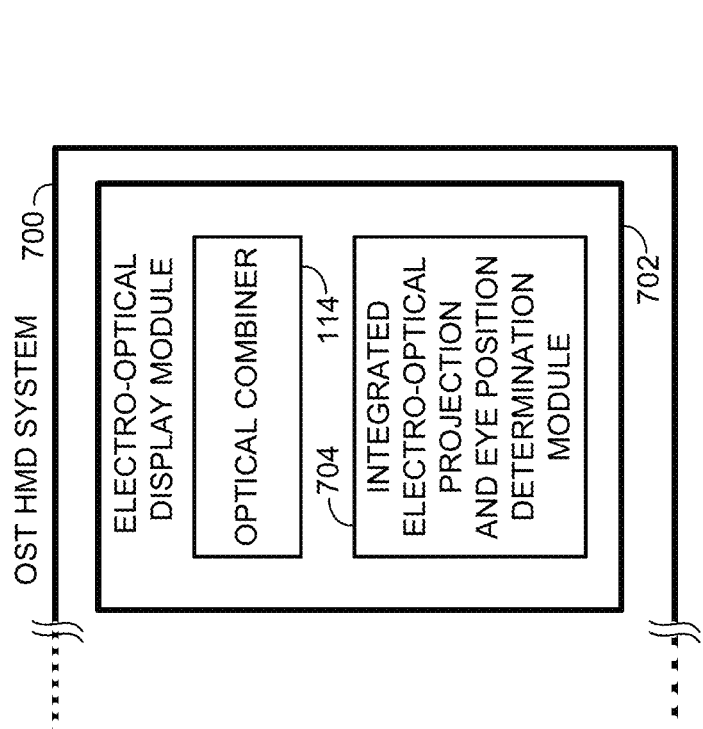
FIG. 10A is a schematic illustration of a partial block diagram of an OST HMD system, showing an integrated electro-optical projection and eye position determination module, constructed and operative in accordance with another embodiment of the disclosed technique.
Figure 10B:
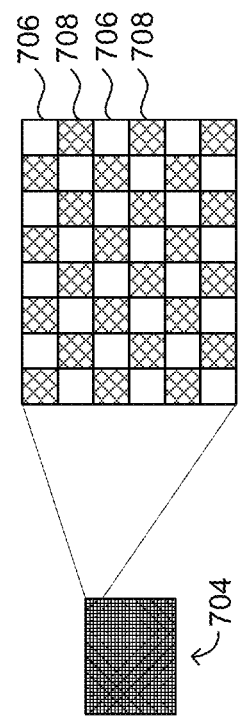
FIG. 10B is a schematic illustration of an example implementation of the integrated electro-optical projection and eye position determination module, of FIG. 10A in greater detail.

In accordance with another embodiment of the disclosed technique, electro-optical projection module 112 and eye position determination module 108 are embodied as a single integrated device. To further elucidate the particulars of this embodiment, reference is made to FIGS. 10A, 10B, and 10C. FIG. 10A is a schematic illustration of a partial block diagram of an OST HMD system, generally referenced 700, showing an integrated electro-optical projection and eye position determination module, constructed and operative in accordance with another embodiment of the disclosed technique. FIG. 10B is a schematic illustration of an example implementation of the integrated electro-optical projection and eye position determination module of FIG. 10A in greater detail. FIG. 10C is a schematic illustration showing a high-level configuration and operation aspects of the OST HMD system of FIG. 10A.

OST HMD system 700 is identical to OST HMD system 100 (FIG. 2) apart from electro-optical display module 110 (of FIG. 2). In particular, OST HMD system 700 includes optical combiner 114 and an integrated electro-optical projection and eye position determination module 704. Integrated electro-optical projection and eye position determination module 704 integrates (the functionality and operation) of electro-optical display module 110 and eye position determination module 108 into a single unit (partly for the purposes of saving space, weight, complexity, and the like). FIG. 10A shows a partial inventory of OST HMD system 700 containing only the relevant differential modifications with respect to OST HMD system 100 (FIG. 2).

FIG. 10B shows an example implementation of the structure and configuration of integrated electro-optical projection and eye position determination module 704 in greater detail. In such an integrated device there is a plurality of discrete light detection elements and a plurality of light emission elements. The light detection elements are configured and operative as light detection elements 708 such as camera photodiodes (represented by as shaded areas in FIG. 10B). The light emission elements are configured and operative as light emission elements 706 (pixels) (represented by non-shaded areas in FIG. 10B). The combined configuration and operation of the camera photodiodes 708 constitute an image sensor that act as a camera enabling to determine eye position of the user (similarly as eye position determination module 108). The combined configuration and operation of the display photodiodes 706 or pixels constitute an electro-optical display configured and operative to irradiate an image for viewing by at least one eye of the user. Integrated electro-optical projection and eye position determination module 704 is capable of acquiring images as well as displaying images synchronized alternately. An example implementation of such an integrated device is a bi-directional organic light emitting diode (OLED) micro display made by the Fraunhofer Institute (specifically, the Fraunhofer Center for Organics, Materials, and Electronic Devices Dresden (COMEDD)). This aspect of the disclosed technique may be implemented by a plurality of integrated electro-optical projection and eye position determination modules 304 (not shown) (e.g., to more accurately determine eye position). In one implementation (not shown), there are a plurality of integrated electro-optical projection and eye position determination modules 304 for one eye. In another implementation (not shown), there is integrated electro-optical projection and eye position determination module 304 for every eye.

Integrated electro-optical projection and eye position determination module 704 is configured and operative to determine at least one eyeball feature position of eye 14 of user 10 wearing OST HMD 700 (diagrammatically represented by light ray 710), to generate corresponding eyeball feature position data, and provide (e.g., transmit) the eyeball feature position data to processor 102 (FIG. 2). Simultaneously, integrated electro-optical projection and eye position determination module 704 is configured and operative to irradiate and project light encoded with information (e.g., an image 714, whose light rays are diagrammatically represented by FIG. 10C by light rays 712 impinging and at least partially reflecting from partially reflective partially transmissive optical element 114) for viewing by at least one eye 14 of user 10 wearing OST HMD system 700. Processor 102 (FIG. 2) provides an image 716 that has been pre-distorted to integrated electro-optical projection and eye position determination module 704, based on unified correction data 370 (FIG. 6E), in accordance with the principles of the disclosed technique heretofore described. The use of integrated electro-optical projection and eye position determination module 704 may be advantageous in enabling the capture of images of the eye from its gazing direction (i.e., which is advantageous in itself for registering the various eye features, as there are substantially no obscurations as in the case where the camera is oriented toward the side of the eye, but the eye is gazing exactly toward the camera). Hence, the determination of at least one eyeball feature position and the generation and irradiation of the images is performed along a common optical axis.

In addition, integrated electro-optical projection and eye position determination module 704 reduces occupied volume, weight and power consumption of the device in comparison with the use of disjoint units, electro-optical projection module 112, and eye position determination module 108 (FIG. 2).

Figure 11B:
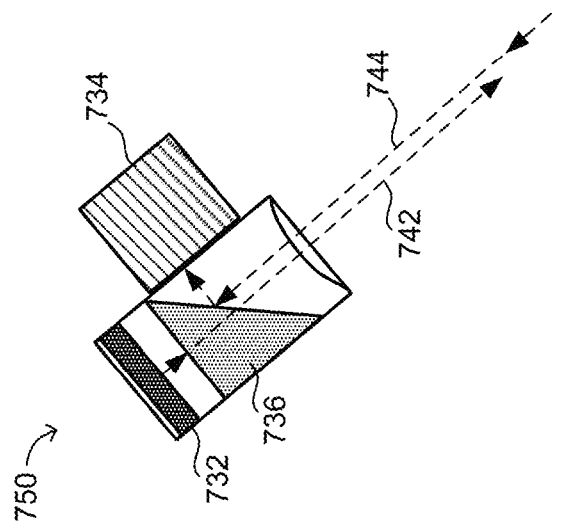
FIG. 11B is a schematic illustration showing the optical configuration of FIG. 11A in greater detail.
Figure 11A:
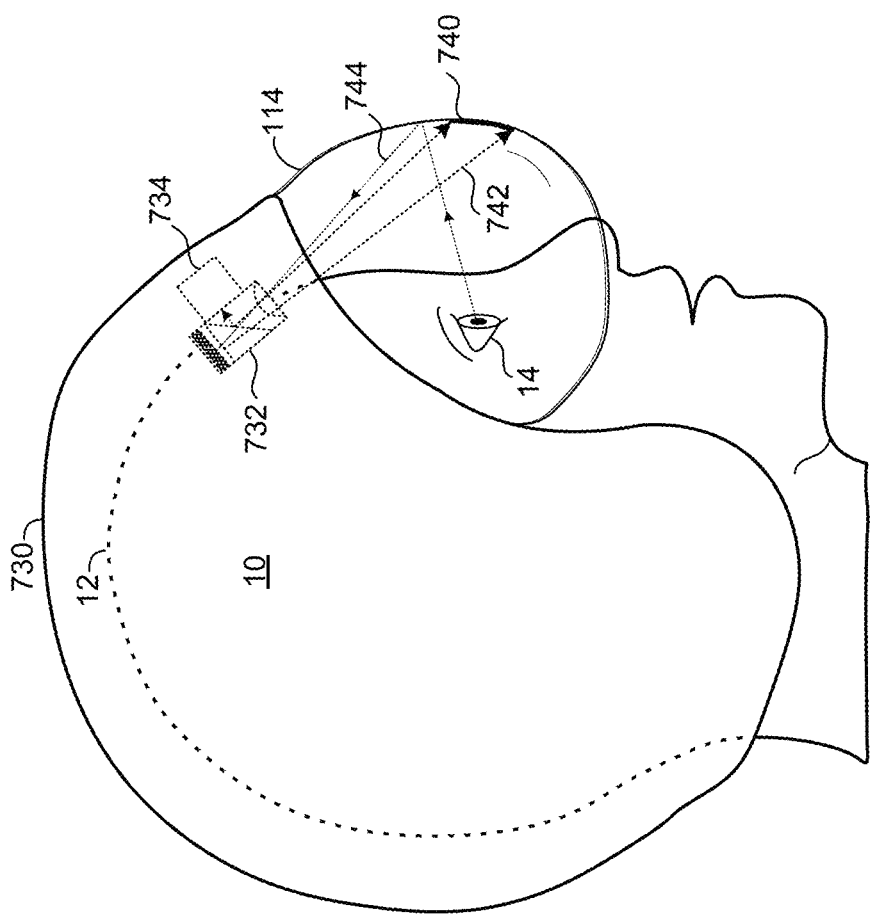
FIG. 11A is a schematic illustration showing another optical configuration of electro-optical projection module and eye position determination module, constructed and operative in accordance with a further embodiment of the disclosed technique.

In accordance with a further embodiment of the disclosed technique, the electro-optical projection module and eye position determination module are configured and operative to have an on-axis optical arrangement. To further elaborate the particulars of this embodiment, reference is now made to FIGS. 11A and 11B. FIG. 11A is a schematic illustration showing another optical configuration of electro-optical projection module and eye position determination module, constructed and operative in accordance with a further embodiment of the disclosed technique. FIG. 11B is a schematic illustration showing the optical configuration of FIG. 11A in greater detail.

FIG. 11A shows OST HMD 730 is substantially similar to OST HMD 100 (FIG. 3), in construction and operation, apart from optical configuration 750 of electro-optical projection module 112 and eye position determination module 108. OST HMD 730 includes an electro-optical projection module 732 (i.e., substantially similar to electro-optical projection module 112 of FIGS. 2 and 3), an eye position determination module 734 (i.e., substantially similar to eye position determination module 108 of FIGS. 2 and 3), and an optical fold 736. Optical fold 736 may be embodied in the form of a prism, a partially transmissive partially reflective mirror, etc. Optical configuration 750 (FIG. 11B) illustrates an on-axis optical arrangement of electro-optical projection module 732 and eye position determination module 734. Electro-optical projection module 732 is configured and operative to project an image 740 onto optical combiner 114, as diagrammatically represented by light rays 742. Eye position determination module 734 is configured and operative to determine at least one eyeball feature position of eye 14 of user 10, by at least one of active techniques (e.g., reflection of projected IR or visible light and detection via at least one camera) and passive techniques (e.g., via detection of at least one camera), as diagrammatically represented by light rays 744. Optical fold 736 is configured and operative to transmit there-through light beams from electro-optical projection module 732 (i.e., light rays 742 toward optical combiner 114), and concurrently reflect externally incoming light beams (i.e., light rays 744) from optical combiner 114 toward eye position determination module 734.

Figure 12B:
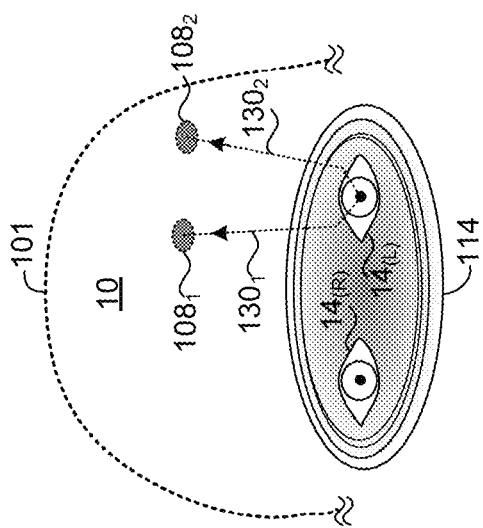
FIG. 12B is a schematic illustration showing a partial forward facing view of OST HMD of FIG. 12A.
Figure 12A:
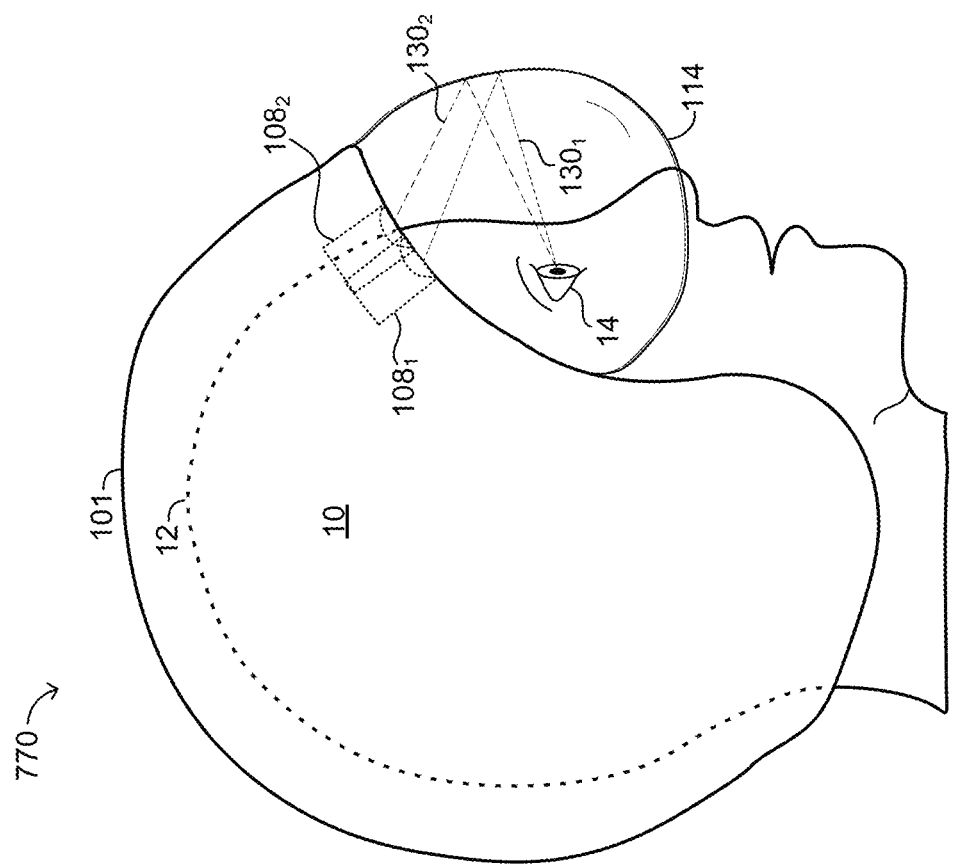
FIG. 12A is a schematic illustration showing a side-view arrangement, of OST HMD, having multiple eye position determination modules, constructed and operative in accordance with another embodiment of the disclosed technique.

In accordance with another embodiment of the disclosed technique, there is provided a configuration incorporating multiple eye position determination modules arranged at different spatial positions with respect to the OST HMD (where the determination of at least one eyeball feature position is performed separately from at least two different spatial positions). To further elaborate the particulars of this embodiment, reference is now made to FIGS. 12A and 12B. FIG. 12A is a schematic illustration showing a side-view arrangement, of OST HMD, generally referenced 770, having multiple eye position determination modules, constructed and operative in accordance with another embodiment of the disclosed technique. FIG. 12B is a schematic illustration showing a partial forward facing view of OST HMD of FIG. 12A.

FIG. 12A illustrates an OST HMD configuration 770 that includes a plurality of eye position determination modules $108_1$ and $108_2$, each of which is operative to determine at least one eyeball feature position of eye 14 of user 10. This embodiment of the disclosed technique is substantially similar to the embodiment described in conjunction with FIG. 3, apart from the employment of multiple eye position determination modules $108_1$ and $108_2$. Although only two eye position determination modules $108_1$ and $108_2$ are shown in FIGS. 12A and 12B, for the sake of simplicity, there can be an arbitrary number thereof, whose configuration and operating principles likewise apply thereto. Analogously, for each eye ($14_L$ or $14_R$—FIG. 12B) there can be assigned at least one eye position determination module for detecting at least one eyeball feature position for the respective eye. This implementation is useful in the case where there is a display module provided for each eye, and each display module is associated separately and respectively with a reference frame (e.g. an HMD having a particular degree of freedom accounting for a change to the interpupillary distance (IPD)). In accordance with the current embodiment, each eye position determination module $108_1$ and $108_2$ is coupled (not shown) with processor 102 (FIG. 2). Multiple eye position determination modules are used to enhance the accuracy of eye position determination (e.g., better discernment of depth or other coordinate(s)). Each eye position determination module $108_1$ and $108_2$ may use passive and/or active detection techniques, as noted hereinabove. Light rays $130_1$ and $130_2$ represent exemplary and respective light paths traversed in the eye position detection of eye position detection modules $108_1$ and $108_2$. The multiple eye position determination modules may be of the same type (e.g., camera-based techniques having at least one light illumination source). Alternatively, the multiple eye position determination modules are of different types. For example, two eye position determination modules, where one is camera-based, the other is laser scanning (and sensing) based.

Alternatively, eye position determination modules $108_1$ and $108_2$ are coupled with each other in a cascaded configuration (not shown), such that the determination of eye position outputted by one eye position determination module is used to refine or augment the output of the other eye position determination module, so as to produce an enhanced eye determination output. In such a configuration only one eye position determination module (or not all) may be coupled with processor 102 (not shown).

Figure 13A:
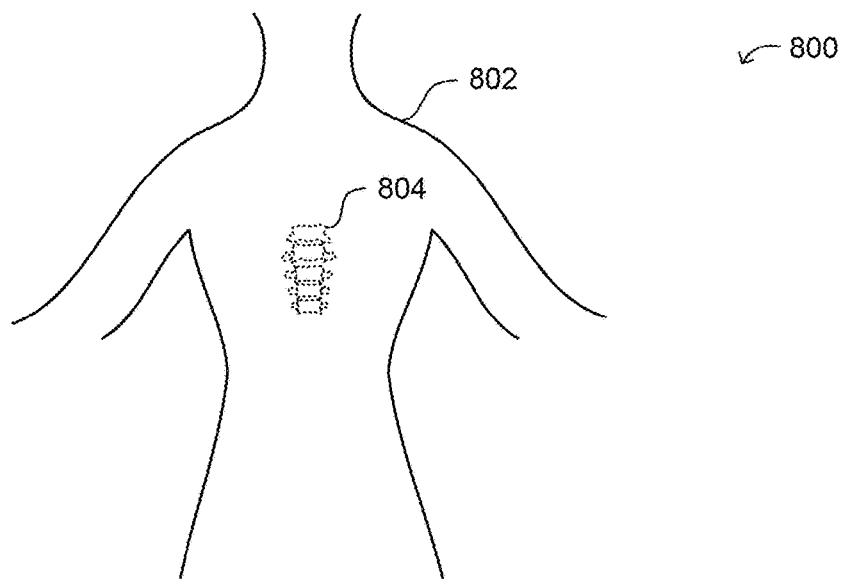
FIG. 13A is a schematic illustration of an example implementation of the disclosed technique in a surgery setting, targeting a hidden object that is an internal body part of a subject.
Figure 13B:
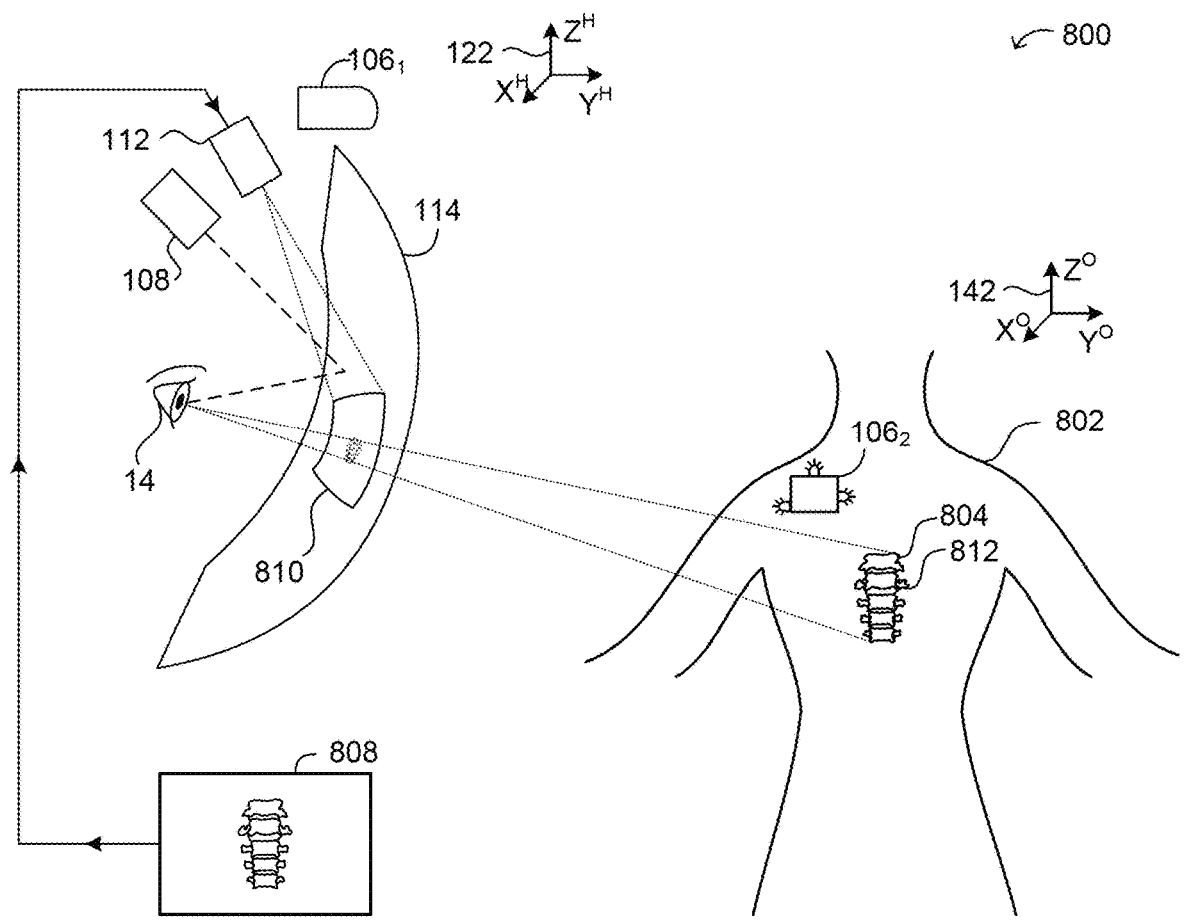
FIG. 13B is a schematic illustration of the surgery setting of FIG. 13A, showing a projected image of the hidden internal body part of 10 the subject being superimposed in an aligned manner with a corresponding position of the hidden internal body part of the subject.

According to the disclosed technique, the image that is projected to the user appears to the user superimposed in an aligned manner with respect to an externally viewed object. The object can be either completely viewable to the user (e.g., unobstructed, exposed, bare, visible, etc.), completely hidden to the user (e.g., totally obstructed, concealed, invisible, etc.), or at least partially hidden and partially viewable (e.g., only partially appearing outwardly that is partly visible and partly invisible). The object may be a physical object (e.g., composed of at least one material), a synthetic or virtual object (e.g., a computer-generated and projected image), etc. To further demonstrate an example implementation of the system and method of the disclosed technique in a case of a hidden object, reference is now made to FIGS. 13A and 13B. FIG. 13A is a schematic illustration of an example implementation of the disclosed technique in a surgery setting, generally referenced 800, targeting a hidden object that is an internal body part of a subject. FIG. 13B is a schematic illustration of the surgery setting of FIG. 13A, showing a projected image of the hidden internal body part of the subject being superimposed in an aligned manner with a corresponding position of the hidden internal body part of the subject.

FIGS. 13A and 13B show a subject 802 (e.g., a patient) in a surgery setting targeted for a medical procedure of an internal body part (i.e., an object) (e.g., vertebrae in this example) 804 that is hidden from view to a user (e.g., a surgeon, a medical practitioner, etc.) of the system and method of the disclosed technique. For example, internal body part 804 is targeted for the medical procedure (e.g., surgery). Further shown in FIG. 13B is tracking system 106 including two distinct units $106_1$ and $106_2$. First unit $106_1$ of the tracking system is mounted on HMD OST 100 (FIG. 3) and is associated with optical assembly reference frame 122. Second unit $106_2$ of the tracking system, associated with object reference frame 142, is rigidly coupled with subject 802 (e.g., to part of a skeleton or bone) such that the position and orientation of second unit $106_2$ is known with respect to the position and orientation of hidden object 804 (e.g., via medical imaging techniques, such as computed tomography (CT) scan, magnetic resonance imaging (MRI), etc.). Tracking system 106 enables registration between the real-world view as seen by the user and a projected image augmenting the real-world view.

FIG. 13B illustrates an eye 14 of the user viewing subject 802 through optical combiner 114. Eye position determination module 108 is configured to determine at least one eyeball feature position of eye 14, according to the embodiments heretofore described. Electro-optical projection module 112, which is associated with second reference frame 122, is configured to irradiate and project an image 808 provided by processor 102 (FIG. 2) for viewing by the user wearing OST HMD 100 (FIG. 1). As noted hereinabove with respect to FIG. 3, the respective positions and/or orientations between tracking system (units $106_1$ and $106_2$) and other helmet-mounted components of system 100, such as eye position determination module 108, electro-optical projection module 112, and optical combiner 114, are known. Processor 102 provides to electro-optical projection module 112 image 808 that has been corrected (according to embodiments heretofore described), using unified correction data 370 (FIG. 6E) that takes into account OST aberration correction (see-through corrections), and electro-optical projection module and optical combiner aberrations (display corrections). Projected image 808 at least partially reflected off 810 optical combiner 114 is seen by eye 14 of user in an aligned manner on subject 802 such that an image of hidden object 812 is superimposed on the position of hidden object 804. Tracking system 106 determines the distance between OST HMD 100 and hidden object 804 so that image of hidden object 812 is correspondingly scaled to match respective dimensions of hidden object 804. Tracking system 106 is configured and operative to determine the relative orientation between first unit $106_1$ (associated with optical assembly reference frame 112) and second unit $106_2$ (associated with object reference frame 142) so that image of hidden object 812 is correspondingly oriented to match the respective orientation of hidden object 804.

It will be appreciated by persons skilled in the art that the disclosed technique is not limited to what has been particularly shown and described hereinabove. Rather the scope of the disclosed technique is defined only by the claims, which follow.

The invention claimed is:

1. An optical see-through (OST) head mounted display (HMD) system, for viewing an image aligned with an object associated with a first reference frame, the OST HMD system comprising:
   an electro-optical display module including:
      at least one partially reflective partially transmissive optical element for at least one of viewing therethrough said object, and viewing said image; and
      at least one electro-optical projection module configured to irradiate said image for viewing by at least one eye of a user who wears said OST HMD, said electro-optical display module being associated with a second reference frame; and
   a processor configured to be coupled with said electro-optical display module, said processor configured to generate said image, according to predetermined information, eyeball feature position data, and at least one of an orientation, and a position and orientation, so that said image appears to said user in an aligned manner with respect to said object;
   wherein said eyeball feature position data is associated with at least one eyeball feature position of said at least one eye, with respect to said second reference frame;
   wherein said at least one of orientation, and position and orientation is of said second reference frame with respect to said first reference frame; and
   wherein said predetermined information relates correction data of said OST HMD to a plurality of different respective position data values of said at least one eyeball feature position;
   wherein said predetermined information further includes display corrections of said electro-optical display module with respect to said position data values of said at least one eyeball feature position,
   wherein said predetermined information further includes see-through corrections of said at least one partially reflective partially transmissive optical element,
   wherein said predetermined information is attained via a calibration procedure with respect to said plurality of different respective position data, using a calibration system,
   wherein said object is either one of at least partially appearing outwardly and completely hidden to said user through said at least one partially reflective partially transmissive optical element when said image is irradiated by said at least one optical projection module.

2. The system according to claim 1, further comprising a position determination module, configured to determine said at least one eyeball feature position of said at least one eye with respect to said second reference frame, and to generate corresponding said eyeball feature position data.

3. The system according to claim 2, wherein said electro-optical display module and said position determination module are mechanically coupled.

4. The system according to claim 2, wherein said electro-optical display module and said position determination module are configured as an on-axis optical arrangement.

5. The system according to claim 1, further comprising a tracking system configured to determine said at least one of an orientation, and a position and orientation, of said second reference frame with respect to said first reference frame.

6. The system according to claim 1, further including a memory device for storing said predetermined information, wherein said processor is configured to read said predetermined information from said memory device.

7. The system according to claim 1, wherein in case said at least one eyeball feature position of said at least one eye does not precisely correspond with one of said plurality of different respective position data values of said predetermined information, said processor is configured to derive from said correction data, closest-matching correction data associated with at least one closest matching position.

8. The system according to claim 1, wherein said OST HMD is used for surgical applications where said hidden object is an anatomical feature.

9. A method for irradiating an image in an optical see-through (OST) head mounted display (HMD) for viewing through the OST HMD an object having at least one of a known orientation and a known position and orientation, with respect to a first reference frame, by at least one eye of a user, the method comprising:
   an initial calibration procedure for acquiring predetermined information with respect to a plurality of different respective eyeball feature position data;
   generating and irradiating said image for viewing by said user, such that said image appears to said user superimposed in an aligned manner with respect to said object that is either one of at least partially appearing outwardly and completely hidden to said user, according to said predetermined information, said eyeball feature position data, and at least one of an orientation, and a position and orientation;
   wherein said predetermined information relates correction data of said OST HMD with a plurality of different respective position data values of at least one eyeball feature position of said at least one eye;
   wherein said predetermined information further includes display corrections of said electro-optical display module with respect to said position data values of said at least one eyeball feature position,
   wherein said predetermined information further includes see-through corrections of said at least one partially reflective partially transmissive optical element,
   wherein said eyeball feature position data is associated with at least one eyeball feature position of said at least one eye, with respect to a second reference frame; and
   wherein said at least one of orientation and position and orientation is of said second reference frame with respect to said first reference frame.

10. The method according to claim 9, further comprising generating said eyeball feature position data, by determining corresponding said at least one eyeball feature position.

11. The method according to claim 10, further comprising deriving closest-matching correction data in case determined said at least one eyeball feature position of said at least one eye does not precisely correspond with one of said plurality of different respective position data values of said predetermined information.

12. The method according to claim 10, wherein said determining said at least one eyeball feature position and generating and irradiating said image is performed along a common optical axis.

13. The method according to claim 10, wherein said determining said at least one eyeball feature position is performed separately from at least two different spatial positions.

14. The method according to claim 9, further comprising determining said at least one of an orientation, and a position and orientation, of said second reference frame with respect to said first reference frame.

15. The method according to claim 9, further comprising storing said predetermined information.

* * * * *